(12) United States Patent
Kim

(10) Patent No.: US 10,631,534 B2
(45) Date of Patent: Apr. 28, 2020

(54) METHOD FOR PRESERVING ACTIVATED PLATELET

(71) Applicant: Hong Seung Kim, Goyang-si (KR)

(72) Inventor: Hong Seung Kim, Goyang-si (KR)

( * ) Notice: Subject to any disclaimer, the term of this patent is extended or adjusted under 35 U.S.C. 154(b) by 0 days.

(21) Appl. No.: 15/899,080

(22) Filed: Feb. 19, 2018

(65) Prior Publication Data

US 2018/0168143 A1 Jun. 21, 2018

Related U.S. Application Data

(62) Division of application No. 15/001,943, filed on Jan. 20, 2016, now Pat. No. 10,015,959.

(30) Foreign Application Priority Data

Jan. 21, 2015 (KR) .................. 10-2015-0010167

(51) Int. Cl.
*A01N 1/02* (2006.01)
*C12N 5/078* (2010.01)

(52) U.S. Cl.
CPC ......... *A01N 1/0226* (2013.01); *C12N 5/0644* (2013.01)

(58) Field of Classification Search
CPC ...... A01N 1/0226; A01N 1/02; A01N 1/0221; A01N 1/0215; C12N 5/0644; C12N 15/111; C12N 15/1131; C12N 15/1132; C12N 2310/14; C12N 2320/11; C12N 2330/10; C12N 2740/16022; C12N 2500/36; C12N 2501/135; C12N 2501/11; C12N 2501/39; C12N 5/0605; C12N 2500/25; C12N 2500/42; C12N 2533/52; C12N 5/0607; C12N 2500/05; C12N 2500/38; C12N 2501/105; C12N 2501/115; C12N 2501/119; C12N 2501/33; C12N 2501/999; C12N 5/0664; C12N 1/04; C12N 2500/02; C12N 2500/10; C12N 2500/32; C12N 2500/34; C12N 2500/40; C12N 2501/01; C12N 2501/392; C12N 5/00; C12N 5/0621; C12N 5/0693; C12N 5/0667; C12N 2502/1305; C12N 2502/1311; C12N 2502/28; C12N 15/113; C12N 15/115; C12N 2310/141; C12N 2310/16; C12N 2310/3513; C12N 2310/3515; C12N 2310/531; C12N 2320/10; C12N 2320/30; C12N 2320/32; C12N 2501/602; C12N 2501/603; C12N 2501/604; C12N 2501/605; C12N 2510/00; C12N 5/0696; C12N 9/2402; C07K 14/005; C07K 14/47; C07K 14/475; C07K 14/49; C07K 14/50; C07K 14/503; C07K 14/65; C07K 16/2803; C07K 16/2827; C07K 16/2896; C07K 16/30; C07K 16/3069; Y02A 90/26; A61K 2300/00; A61K 35/50; A61K 35/644; A61K 38/21; A61K 45/06; A61K 2035/122; A61K 9/0019; A61K 33/04; A61K 31/195; A61K 33/30; A61K 31/10; A61K 35/12; A61K 9/127; A61K 38/063; A61K 38/1709; A61K 38/1825; A61K 38/1858; A61K 38/30; A61K 8/02; A61K 8/4933; A61K 8/64; A61K 8/98; A61K 9/0026; A61K 2039/6025; A61K 39/0011; A61K 49/0043; A61K 49/0058; A61K 49/0089; A61K 35/19; A61F 2/062; A61L 2430/20; A61L 27/38; A61L 27/3895; A61L 27/507; C01B 15/04; C01B 15/043; C01B 15/047; C12M 21/08; C12M 25/14; C12M 29/12; C12M 29/14; Y10S 428/917; Y10S 623/916; Y10S 623/921; Y10S 977/773; Y10S 977/774; Y10S 977/775; Y10S 977/776; Y10S 977/777; Y10S 977/81; Y10S 977/811; Y10S 977/896; Y10S 424/04; Y10S 514/852; Y10S 514/912; Y10T 428/26; Y10T 428/2982; Y10T 428/2991; Y10T 428/31; Y10T 428/315; A61P 17/14; A61Q 5/006; A61Q 5/02; A61Q 7/00;

(Continued)

(56) References Cited

U.S. PATENT DOCUMENTS 10,015,959 B2 * 7/2018 Kim .................. A01N 1/0226
2015/0004694 A1 1/2015 Mayaudon et al.

FOREIGN PATENT DOCUMENTS

KR 10-2014-0045822 A 4/2014
WO 2014007422 A1 1/2014

OTHER PUBLICATIONS

Burk et al, "Plasma selenium in specific and non-specific forms", Biofactors. 2001; 14(1-4):107-14. 2001.*

(Continued)

*Primary Examiner* — Deborah K Ware
(74) *Attorney, Agent, or Firm* — Bracewell LLP; Brad Y. Chin

(57) ABSTRACT

Embodiments relate to an activated platelet preservation composition, a method for preserving activated platelet, and a preserved activated platelet using the same. According to at least one embodiment, there is provided an activated platelet preservation composition including a divalent cation, chloride, vitamin B, a selenium source and a solvent, a kit using the same, a method for preserving an activated platelet, and a preserved activated platelet using the same. According to various embodiments, it is possible to obtain and preserve platelets, which are positive for CD61 and CD62p and negative for PAC-1 among cell markers.

2 Claims, 36 Drawing Sheets
(36 of 36 Drawing Sheet(s) Filed in Color)

(58) Field of Classification Search
CPC ............... C12Q 1/6886; C12Q 1/6804; C12Q 2600/118; C12Q 2600/156; C12Q 2600/158; C12Q 2600/178; G01N 2500/00; G01N 2500/10; G01N 33/5011; G01N 33/5082; G01N 33/574; G01N 33/5076; G01N 33/53; G01N 33/57407; G01N 33/57488; G01N 33/6863; A61J 1/10; C12Y 302/01018
See application file for complete search history.

(56) References Cited

OTHER PUBLICATIONS

Conway, et al.; Prognostic Value of Plasma van Willebrand Factor and Soluble P-Selectin as Indices of Endothelial Damage and Platelet Activation in 994 Patients with Nonvalvular Atrial Fibrillation; Circulation AHA Journal; Jul. 1, 2003; pp. 3141-3145.

Wu, et al.;Inhibitory role of S-nitrosoglutathione in the aggregation of frozen platelets, and its effect on the expression of membrane glycoproteins; Experimental and Therapeutic Medicine 6: 831-839, 2013.

Sandgren, et al.;Storage of buffy-coat-derived platelets in additive solution: in vitro effects on platelets of the air bubbles and foam included in the final unit; Blood Transfus 9:182-8, 2011.

* cited by examiner

METHOD FOR PRESERVING ACTIVATED PLATELET

CROSS-REFERENCE TO RELATED APPLICATIONS

This application is a divisional of U.S. patent application Ser. No. 15/001,943, filed Jan. 20, 2016, which claims priority of Korean Patent Application No. 10-2015-0010167, filed on Jan. 21, 2015, in the Korean Intellectual Property Office, which is hereby incorporated by reference in its entirety.

BACKGROUND

Field

Embodiments relate to an activated platelet preservation composition, a method for preserving activated platelets and a preserved activated platelet using the same. In particular, embodiments relate to an activated platelet preservation composition, which can preserve activated platelets expressing CD61 and CD62p, but not expressing PAC-1 among cell markers, a method for preserving activated platelets using the same and preserved activated platelets using the same.

Description of Related Art

Interest in blood supply has been continuously increasing worldwide. However, because the storage stability of blood products is relatively short, now, the storage period of concentrated red blood cells, blood products for blood transfusions and the like, is mostly limited. After the limited storage period, the pH of concentrated red blood cells becomes very low and the ATP level thereof decreases rapidly at the same time, and circulation life is significantly reduced during blood transfusions.

It is known that red blood cells can generally be stored for up to 35 days, and in particular, platelets are produced in the body's bone marrow and can survive about for 7 days in vivo, but after blood collection, the storage period thereof is generally much shorter than other blood products.

When platelets in the blood are separated from the body and preserved, spontaneous activation occurs, and it is known that this spontaneous activation occurs by changes in shear force during blood collection by venipuncture, use of anticoagulants such as citrates, heparin and the like for centrifugation or platelet separation, preservation containers, temperature and the like.

Like this, it is known that when the spontaneous activation of platelets occurs, platelets are aggregated, and many kinds of growth factors and cytokines are synthesized in alpha-granules of platelets.

However, when platelets are separated from the body, platelet destruction occurs simultaneously with the spontaneous activation, and at this time, platelets are degraded into microparticles. Thus, when measuring platelets using a flow cytometry method, they are no longer measured, and a platelet count is reduced. For this reason, it is known that platelets cannot be preserved for 5 days or longer when preserved in vitro. Except for the 24 hours to 48 hours taken to separate platelets from the blood, the actual storage life is only 3 to 4 days.

Meanwhile, a representative marker of platelets is CD61, and CD61 is a platelet marker expressed in both activated platelets and inactivated platelets, but not expressed in microparticles. Thus, it is used as a platelet marker.

Furthermore, specific representative markers of the activated platelets are PAC-1 and CD62P (P-selectin), and the PAC-1 is a ligand for Gp IIb-IIIa involved in platelet aggregation. Thus, it is known that PAC-1 is involved in platelet aggregation, degradation into microparticles and apoptosis, but is not related to activation of granules in a cell. On the other hand, CD62P is a cell marker used as an indicator of leukocyte activation and granule activation of platelets.

Thus, if a composition or method, which can maintain the state of activated platelets expressing CD61 and CD62p but not expressing PAC-1, among cell markers for an extended period of time, is provided, platelet destruction can be prevented, the spontaneous activation can be maintained, and consequently, activated platelets can be obtained which can be preserved for an extended period of time of time. Thus, it is expected that such a method could be usefully applied in related fields.

SUMMARY

Embodiments of the invention are directed to an activated platelet preservation composition, which can preserve activated platelets expressing CD61 and CD62p but not expressing PAC-1 for an extended period of time.

Embodiments provide a preservation kit for preserving activated platelets for an extended period of time.

An embodiment of the invention directed to a method for preserving activated platelets using the activated platelet preservation composition of the present invention as described above.

Another embodiment of the invention is directed to an activated platelet preserved to express CD61 and CD62p but not express PAC-1.

According to an embodiment, an activated platelet preservation composition comprising a divalent cation, chloride, vitamin B, a selenium source and a solvent is provided.

The activated platelet may be positive for CD61 and CD62P (P-Selectin) cell markers, and negative for a PAC-1 cell marker.

The divalent cation may preferably be at least one selected from the group consisting of $Zn^{2+}$, $Cu^{2+}$, $Mg^{2+}$, and $Cr^{2+}$.

The selenium source may preferably be sodium selenite pentahydrate ($Na_2SeO_3 \cdot 5H_2O$), sodium selenite or a combination thereof.

The chloride may preferably be at least one selected from the group consisting of sodium chloride (NaCl), potassium chloride and bromine chloride.

The vitamin B may be preferably be vitamin B6 (pyridoxine).

The solvent may preferably be distilled water.

The activated platelet preservation composition may preferably comprise the 0.5 mg to 20 mg of the divalent cation, 0.1 mg to 10 mg of the chloride, 1 mg to 5 mg of the vitamin B, 10 mg to 30 mg of the selenium source and a balance of solvent per 2 cc of the total activated platelet preservation composition volume so as to realize a final volume of the total composition of 2 cc.

According to another embodiment of the present invention, an activated platelet preservation kit comprising a sterilized airtight container, which contains the activated platelet preservation composition of the present invention and whose internal pressure is equalized with external pressure, is provided.

According to another embodiment of the present invention, a method for preserving activated platelets, comprising:

mixing blood with an anticoagulant and then centrifuging thereof to obtain platelet rich plasma and plasma; injecting the platelet rich plasma and the plasma obtained above into the sterilized airtight container, which contains the activated platelet preservation composition of the present invention and whose internal pressure is equalized with external pressure; and preserving the container into which the platelet rich plasma and the plasma are injected at a temperature of 35° C. to 38° C., is provided.

The preserving may be maintained for 14 days or longer.

The preserved platelet may preferably be positive for CD61 and CD62P (P-Selectin) cell markers, and negative for the PAC-1 cell marker.

According to another embodiment, an activated platelet, which is positive for CD61 and CD62P (P-Selectin) cell markers, and negative for the PAC-1 cell marker, is provided.

The activated platelet may preferably be preserved by the activated platelet preservation composition of the various embodiments.

BRIEF DESCRIPTION OF DRAWINGS

The patent of application file contains at least one drawing executed in color. Copies of this patent or patent application publication with color drawing will be provided by the office upon request and payment of the necessary fee.

The above and other aspects, features and other advantages of the present disclosure will be more clearly understood from the following detailed description taken in conjunction with the accompanied drawings, in which.

DETAILED DESCRIPTION

Figure 1:
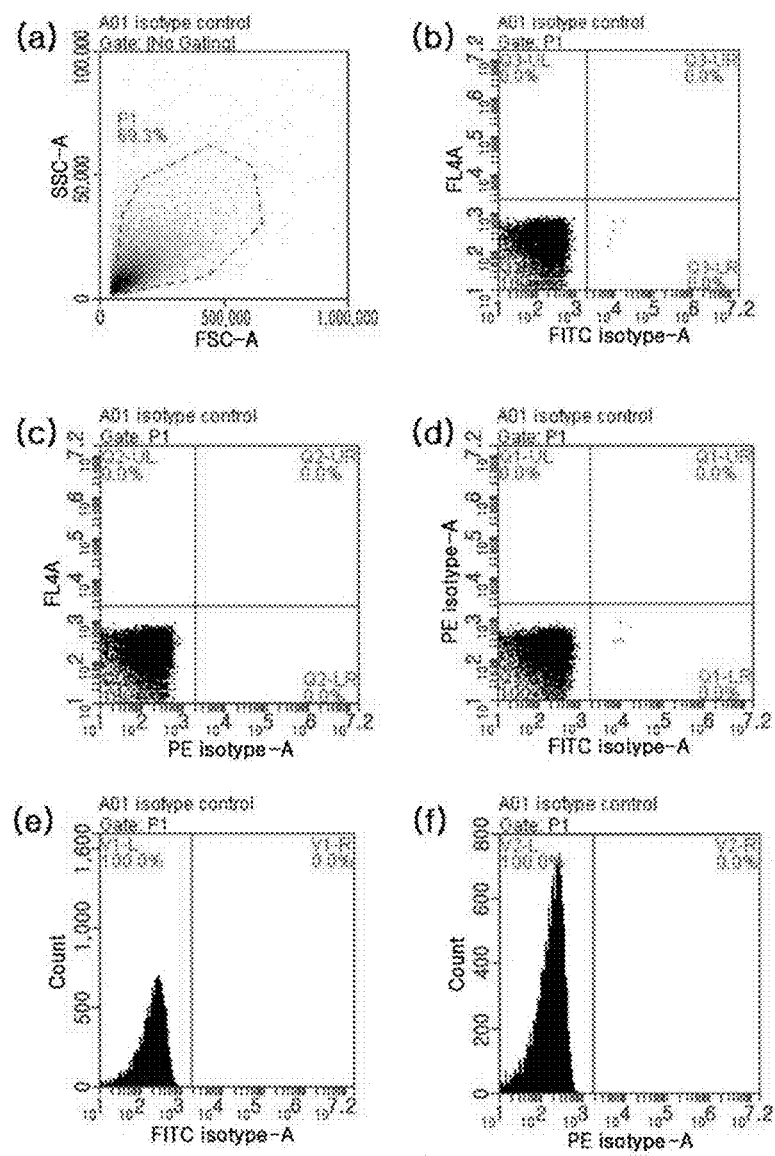
FIG. 1 is the result of flow cytometry for control staining at preservation initiation in case 1.

Hereinafter, embodiments of the present inventive concept will be described as followed referring to the attached drawings.

The present inventive concept may, however, be exemplified in many different forms and should not be construed as being limited to the specific embodiments set forth herein. Rather, these embodiments are provided so that this disclosure will be thorough and complete, and will fully convey the scope of the disclosure to those skilled in the art.

The terminology used herein is for describing particular embodiments only and is not intended to be limiting of the present inventive concept. As used herein, the singular forms "a," "an," and "the" are intended to include the plural forms as well, unless the context clearly indicates otherwise. It will be further understood that the terms "comprises," and/or "comprising" when used in this specification, specify the presence of stated features, integers, steps, operations, members, elements, and/or groups thereof, but do not preclude the presence or addition of one or more other features, integers, steps, operations, members, elements, and/or groups thereof.

According to the present invention, an activated platelet preservation composition, which can preserve activated platelets for an extended period of time and can obtain and maintain platelets positive for, that is expressing, a platelet marker, CD61, and an activation marker, CD62p; and negative for, that is not expressing, PAC-1 among cell markers, is provided.

Here, the activated platelet preservation composition comprises a divalent cation, chloride, vitamin B, a selenium source and a solvent.

In the present invention, the term 'at least one' refers to the fact that each ingredient can be used individually, or used in combination of two or more ingredients.

The divalent cation plays a role in anti-oxidation in the preservation composition of the present invention, and furthermore, it is an ingredient designed to stabilize cell membranes and adjust an electrolyte balance. Preferably, it may be at least one selected from the group consisting of $Zn^{2+}$, $Cu^{2+}$, $Mg^{2+}$, and $Cr^{2+}$, and more preferably, it may be a combination of $Mg^{2+}$ and $Zn^{2+}$. The divalent cation may be contained in the form of a suitable salt known in the art, such as copper sulfate, magnesium sulfate, zinc sulfate and the like, and for example, it may include a combination of zinc sulfate and magnesium sulfate.

The activated platelets of the present invention are positive for CD61 and CD62P (P-Selectin) cell markers, and negative for the PAC-1 cell marker.

Namely, according to the present invention, the activated platelets, which are positive for CD61 and CD62P (P-Selectin) cell markers, and negative for the PAC-1 cell marker, can be obtained, and at this time, the activated platelets may be those preserved by the activated platelet preservation composition of the present invention.

At this time, CD61 is a platelet standard marker as a cell marker related to glycoprotein IIIa on the platelet surface, and a platelet marker expressed in both activated platelets and inactivated platelets, but not expressed in microparticles. Thus, it is used for the platelet marker.

Furthermore, the PAC-1 is a ligand for Gp IIb-IIIa involved in platelet aggregation, and is involved in platelet aggregation, degradation into microparticles and apoptosis. The CD62P is a cell marker used as an indicator of leukocyte activation and granule activation of platelets.

Accordingly, the activated platelets according to the present invention expressing CD61 and CD62p but not expressing the PAC-1 among the cell markers can prevent platelet destruction and maintain spontaneous activation, and in the present invention, the 'activated platelet' means a platelet expressing CD61 and CD62p but not expressing the PAC-1.

The selenium source contained in the activated platelet composition of the present invention may be any compound so long as it supplies selenium without particular limitation, and it may be a salt, hydrate and the like of a selenium compound. A specific example may be sodium selenite pentahydrate ($Na_2SeO_3.5H_2O$), or an inorganic selenium such as sodium selenite, and the sodium selenite pentahydrate is more preferred because it has a stable structure and is released at in vivo pH, thereby activating glutathione dependent de-oxygenase. The glutathione dependent de-oxygenase is an anti-oxidation mechanism of a platelet. Thus, in the case of using the sodium selenite pentahydrate, oxidative stress, that is a major cause of the platelet destruction, can be removed more effectively.

The selenium source of the present invention may preferably be contained in an amount of 10 mg to 30 mg, based on the final volume, 2 cc, of the preservation composition of the present invention, and it may more preferably be contained in an amount of 15 mg to 25 mg. If the selenium source is contained in an amount of less than 10 mg, there may be a problem of cell destruction because an oxidation effect may be insufficient, and if it is contained in an amount of more than 30 mg, there may be a problem of cell membrane toxicity.

In the present invention, the divalent cation may preferably be at least one selected from the group consisting of $Zn^{2+}$, $Cu^{2+}$, $Mg^{2+}$, and $Cr^{2+}$, and it may more preferably be $Zn^{2+}$, $Mg^{2+}$ or a combination thereof.

The divalent cation is an ingredient designed to stabilize cell membranes and adjust electrolyte balance as well as play a role in anti-oxidation in the preservation composition of the present invention to prevent cell destruction caused by oxidative stress by oxides. The divalent cation may be contained in the form of a suitable salt known in the art, such as a sulfate, a citrate and the like, for example, copper sulfate, magnesium sulfate, zinc sulfate and the like. Most preferably, it may include a combination of zinc sulfate and magnesium sulfate.

Preferably, the divalent cation may be contained in the activated platelet preservation composition of the present invention in an amount of 0.5 mg to 20 mg, based on the final volume, 2 cc, of the preservation composition of the present invention, it may more preferably be contained in an amount of 5 mg to 10 mg, and it may further more preferably be contained in an amount of 5.5 mg to 9.8 mg. Most preferably, it may include a combination of zinc sulfate from 0.5 mg to 0.8 mg and magnesium sulfate from 5 mg to 9 mg.

If the divalent cation is contained in an amount of less than 0.5 mg, an anti-oxidation effect may be reduced, and there may be a problem in terms of cell membrane stability due to lowered osmotic pressure, and if it is contained in an amount of 20 mg, there may be a problem of apoptosis caused by high osmotic pressure in the preservation composition.

The chloride contained in the present invention plays a role in maintaining electrical stability of cells by stabilizing cations in the activated platelet preservation composition of the present invention, and properly maintaining concentrations of the preservation composition and the accompanying osmotic pressure. It may preferably be at least one selected from the group consisting of sodium chloride (NaCl), potassium chloride and bromine chloride, and more preferably be potassium chloride or a combination of potassium chloride and sodium chloride.

The chloride may be contained in the preservation composition of the present invention in an amount of 0.1 mg to 10 mg, based on the final volume, 2 cc, of the preservation composition of the present invention, and it may more preferably be contained in an amount of 4 mg to 8 mg. More preferably, it may contain a combination of 0.2 mg to 0.5 mg of sodium chloride and 4 mg to 7 mg potassium chloride.

If the chloride is contained in an amount of less than 0.1 mg, there may be a problem that osmotic pressure is excessively decreased, and if it is contained in an amount of more than 10 mg, there may be a problem that osmotic pressure is excessively increased. In the case that osmotic pressure is excessively decreased or increased as described above, it may negatively influence on platelet preservation, and the activated platelet preservation may not go smoothly.

In particular, the vitamin B may preferably be vitamin B6 (pyridoxine), and the vitamin B plays a role in maintaining the platelet preservation composition stably through an anti-oxidation effect.

The vitamin B may preferably be contained in the preservation composition of the present invention in an amount of 1 mg to 5 mg, based on the final volume, 2 cc, of the preservation composition of the present invention, it may more preferably be contained in an amount of 2 mg to 4 mg, and it may further more preferably be contained in an amount of 1.8 mg to 3.5 mg.

If the vitamin B6 is contained in an amount of less than 1 mg, there may be a problem in maintaining stability of the preservation composition, and if it is contained in an amount of more than 5 mg, there may be a problem of cytotoxicity.

The solvent, which can be used in the present invention, is water, and preferably, it may be distilled water.

The activated platelet preservation composition of the present invention may preferably comprise the 0.5 mg to 20 mg of the divalent cation, 0.1 mg to 10 mg of the chloride, 1 mg to 5 mg of the vitamin B, 10 mg to 30 mg of the selenium source and a balance of solvent per 2 cc of the total activated platelet preservation composition volume to realize a final volume of the total composition of 2 cc.

Meanwhile, according to the present invention, a preservation kit for preserving platelets is provided. The preservation kit of the present invention comprises an airtight container containing the activated platelet preservation composition of the present invention as described above.

Here, the activated platelet preservation kit of the present invention may preferably comprise a sterilized airtight container in which the activated platelet preservation composition of the present invention is included and whose internal pressure is equalized with external pressure.

The container which can be used for the preservation kit of the present invention may be preferably a sterilized airtight container, and material of the container is not particularly limited, and it may be any container so long as it is suitable for preserving platelets, but it may preferably be glass. However, any other suitable container known in the art so long as it can contain the preservation composition stably may be used. Most preferably, it may be a vial.

The container may preferably contain the preservation composition of the present invention in an amount of about 7/50 to 9/50 of the total volume.

Furthermore, according to the present invention, a method for preserving the activated platelets for an extended period of time is provided.

The method of the present invention uses the preservation composition and the preservation kit of the present invention, and in this case, it comprises: mixing blood with an anticoagulant and then centrifuging thereof to obtain platelet rich plasma and plasma; injecting the platelet rich plasma and the plasma obtained above into the sterilized airtight container, which contains the activated platelet preservation composition of the present invention and whose internal pressure is equalized with external pressure; and preserving the container into which the platelet rich plasma and the plasma are injected at a temperature of 35° C. to 38° C.

The preservation composition and the preservation kit comprising thereof, which can be used in the method of the present invention for preserving platelets, is as described above.

Here, in the method for preserving activated platelet of the present invention, first of all, the blood is mixed with the anticoagulant to prevent coagulation of the blood obtained from the human body, and then the mixture is centrifuged to obtain the platelet rich plasma and the plasma including platelets.

At this time, the blood may preferably be peripheral blood obtained from the extremities of the human body. The peripheral blood may more preferably be obtained from veins, for example, veins of the arms, legs and the like.

The anticoagulant, which can be used at this time, may be at least one selected from the group consisting of sodium citrate and heparin, but is not limited thereto.

The anticoagulant is mixed at a ratio of 9 to 11 parts by weight per 100 parts by weight of the peripheral blood, and preferably at a ratio of about 10 parts by weight. If the anticoagulant is mixed in a ratio of less than 9 parts by weight per 100 parts by weight of the peripheral blood, an anticoagulant effect may not be sufficient, and if the anticoagulant is mixed in an amount of more than 11 parts by weight, there may be a problem of occurrence of citrate toxicity.

The centrifugation for blood separation may be conducted within a range of 1500 rpm to 1700 rpm for 20 min to 25 min, and more preferably within a range of 1600 rpm to 1700 rpm for 22 min to 24 min. If the centrifugation is conducted slower than 1500 rpm or for shorter than 20 min, there may be a problem that the centrifugation is insufficiently conducted, and if it is conducted faster than 1700 rpm or for longer than 25 min, there may be a problem about cell damage.

After the centrifugation is completed, the blood is separated into 4 layers. The bottom layer is a layer occupying about 45% to 50% and consisting of red blood cells; the layer above it is a layer occupying about 1% and including white blood cells called 'buffy coat'; and the platelet rich plasma layer and the plasma layer are formed thereon in order and occupying about 49% to 54% of the whole.

The platelet rich plasma layer and the plasma layer separated above are injected into the sterilized airtight container, which contains the preservation composition of the present invention as described above and in which internal pressure is equalized with external pressure. The external pressure is atmospheric pressure, and controlling pressure may be conducted by, for example, a method of passing a syringe needle through a packed rubber stopper and then removing the syringe needle when pressure is balanced, but is not limited thereto.

Subsequently, the container into which the platelet rich plasma layer and the plasma layer are injected is preserved at a temperature of 35° C. to 38° C., and more particularly, may be preserved at a temperature of about 37° C. If the container is preserved at a temperature of lower than 35° C., there may be problems that the division of platelet precursor cells is deteriorated and platelet preserving efficiency in the preservation composition is reduced, and if it is preserved at a temperature of higher than 38° C., there may be a problem of thermal cell damage.

According to the platelet preserving method according to the present invention, platelets can be preserved in the activated state for at least 14 days, i.e., for a period of 2 weeks or longer, and the preserved platelets are positive for CD61 and CD62P (P-Selectin) cell markers, and negative for the PAC-1 cell marker.

Hereinafter, the present disclosure will be described more specifically through examples. The following examples are for illustrative purposes only and are not intended to limit the scope and spirit of the present invention.

EXAMPLE

1. Manufacturing of Kit Including Activated Platelet Preservation
Composition

A 50 cc glass bottle was washed clean, dried, packed with a rubber stopper and then double sealed with an aluminum cap. The bottle was treated so the rubber stopper could not be detached therefrom, while air and foreign materials could not enter thereinto followed by being subjected to high pressure sterilization.

2 cc of the activated platelet preservation composition of the present invention was injected into the sterilized and air tightened glass bottle as described above. The activated platelet preservation composition of the present invention was made to include the ingredients in the content of the following Table 1. Here, distilled water was used as a solvent, and the final volume of the total activated platelet preservation composition was adjusted to 2 cc.

TABLE 1

|  | Per 2 cc of Activated Platelet Preservation Composition |
|---|---|
| Sodium Chloride | 0.36 mg |
| Potassium Chloride | 5.6 mg |
| Zinc Sulfate(ZnSo4) | 0.64 mg |
| Sodium Selenite Pentahydrate($Na_2SeO_3 \cdot 5H_2O$) | 23.2 mg |
| Magnesium Sulfate($MgSO_4$) | 6.7 mg |
| Pyridoxine | 2.0 mg |

2. Platelet Separation and Injection into Kit 30 cc of venous blood was collected from veins of 4 candidates, respectively, and mixed with 1.5 cc of an anti-coagulant (sodium citrate 4 g/100 ml), and then centrifuged at a rate of 490 G for about 30 min to separate and extract buffy coat and plasma including platelets. The buffy coat and the plasma were injected into the glass bottle of the kit including the activated platelet preservation composition of the present invention obtained in 1, respectively.

In general, the volume of the buffy coat and the plasma obtained by centrifuging 30 cc of the blood varies depending on hematocrit of each individual, but it is usually about 12 cc to 14 cc. In the present invention, it was just expressed as the plasma and the buffy coat separated from whole blood 30 cc.

3. Platelet Preservation and Preservation Result 4 kits into which platelets obtained from the 4 candidates in 2, were injected and were preserved at a temperature of about 37° C. for 2 weeks, respectively, and platelet count and cell markers, CD61, CD62P and PAC-1, were checked when starting preservation and 2 weeks after preservation, respectively.

(1) Check of Platelet Count (Number)

Analysis of the platelet count when starting preservation in the platelet preservation kit and the platelet count 2 weeks after preservation were requested by Seoul Medical Science Institute foundation and conducted using an automatic blood cell counter (calculator, Beckman coulter LH789 model).

When designating tests for the 4 candidates as case 1 to 4, respectively, Test Examples 1 to 4 of the following Table 2 show the results of the platelet count for platelets obtained from each case.

TABLE 2

|  | 0 Week (When starting preservation) | After 2 Weeks |
|---|---|---|
| Test Example 1 | 216 | 86 |
| Test Example 2 | 307 | 128 |
| Test Example 3 | 388 | 123 |
| Test Example 4 | 202 | 91 |

* Unit: $\times 10^3/uL$

In general, it is known that platelets cannot be preserved for 5 days or longer, but in the case of using the activated platelet preservation composition of the present invention, as can be seen from the above Table 2, it can be confirmed that there are a large number of platelets even 2 weeks after preservation.

Furthermore, whether platelets left after 2 weeks are activated platelets or not is determined in the following test.

(2) Check of Cell Markers, CD61, CD62P and PAC-1

The flow cytometer was a BD Accuri™ C6, and all of the immunofluorescence monoclonal antibodies and reagents used for analyzing the platelet cell markers (Cell Cluster Marker), CD61, CD62P and PAC-1, were BD products. They are listed in the following Table 3.

TABLE 3

| 1 | Isotype antibody against FITC (Cat. No 555748) |
|---|---|
| 2 | Isotype antibody against PE (Cat. No 555749) |
| 3 | FITC monoclonal antibody against CD61 (Cat. No 555753) |
| 4 | PE monoclonal antibody against CD62P (P-selectin) (Cat. No 555524) |
| 5 | FITC monoclonal antibody against PAC-1 (Cat. No 340507) |
| 6 | Fixation buffer (BD Cytofix ™, Cat. No. 554655) |
| 7 | D-PBS (Welgene) |
| 8 | Sodium azide (Sigma) |

First of all, cells were collected by centrifugation at 1000 rpm for 5 min and washed twice with D-PBS, and then cell pellets were re-suspended with D-PBS to obtain the final concentration of $1 \times 10e^7$ cells/m. An antibody was inserted into each tube and incubated while protected from light at ambient temperature for 30 min.

The stained cells were resuspended with D-PBS containing 0.1% sodium azide, and centrifuged at 2000 rpm for 5 min to remove supernatant. Then the stained cells were resuspended with fixation buffer 150 μl and then a sample of the stained cells was analyzed by a flow cytometer. At this time, the analysis was conducted using FACS CELL Quest (BD) program.

The following Test Examples 5 to 8 are about analyzing the results of checking the cell markers, CD61, CD62P and PAC-1, for each platelets obtained from the 4 candidates in the cases 1 to 4.

Test Example 5

Figure 2:
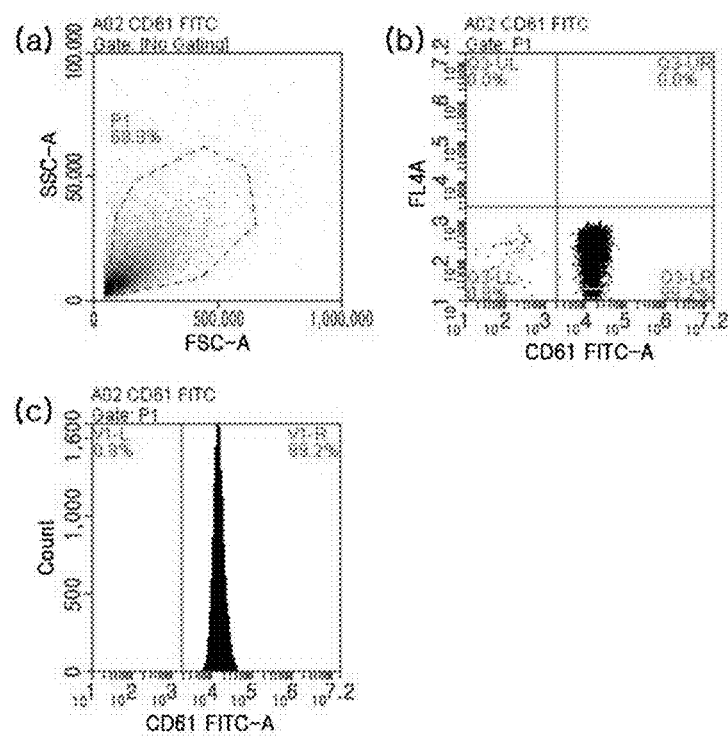
FIG. 2 is the result of flow cytometry for CD61 at preservation initiation in case 1.
Figure 3:
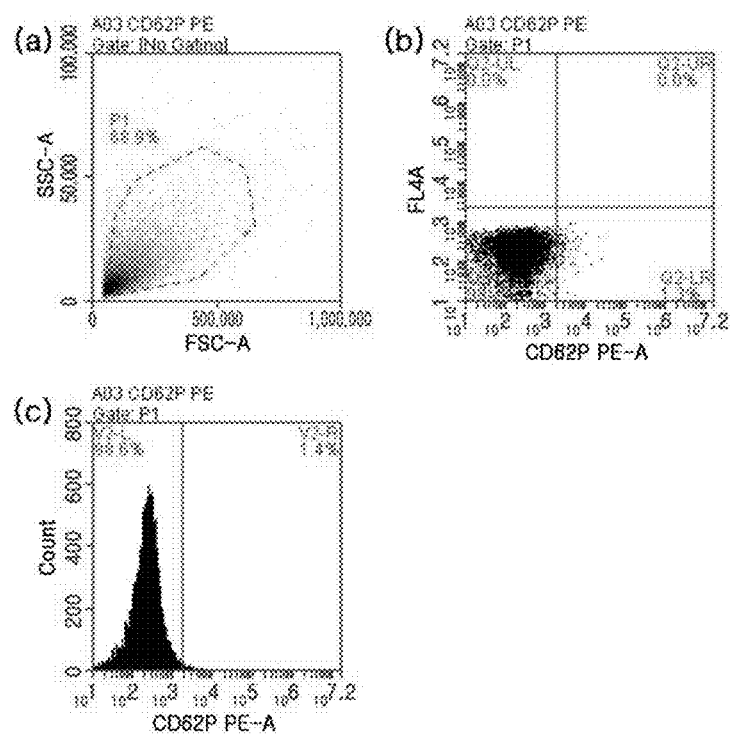
FIG. 3 is the result of flow cytometry for CD62P at preservation initiation in case 1.
Figure 4:
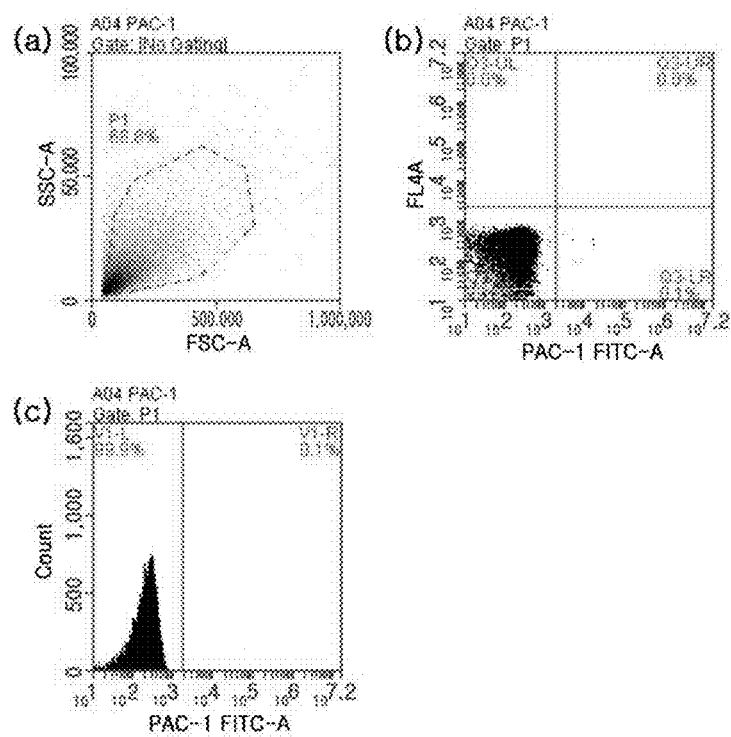
FIG. 4 is the result of flow cytometry for PAC-1 at preservation initiation in case 1.
Figure 5:
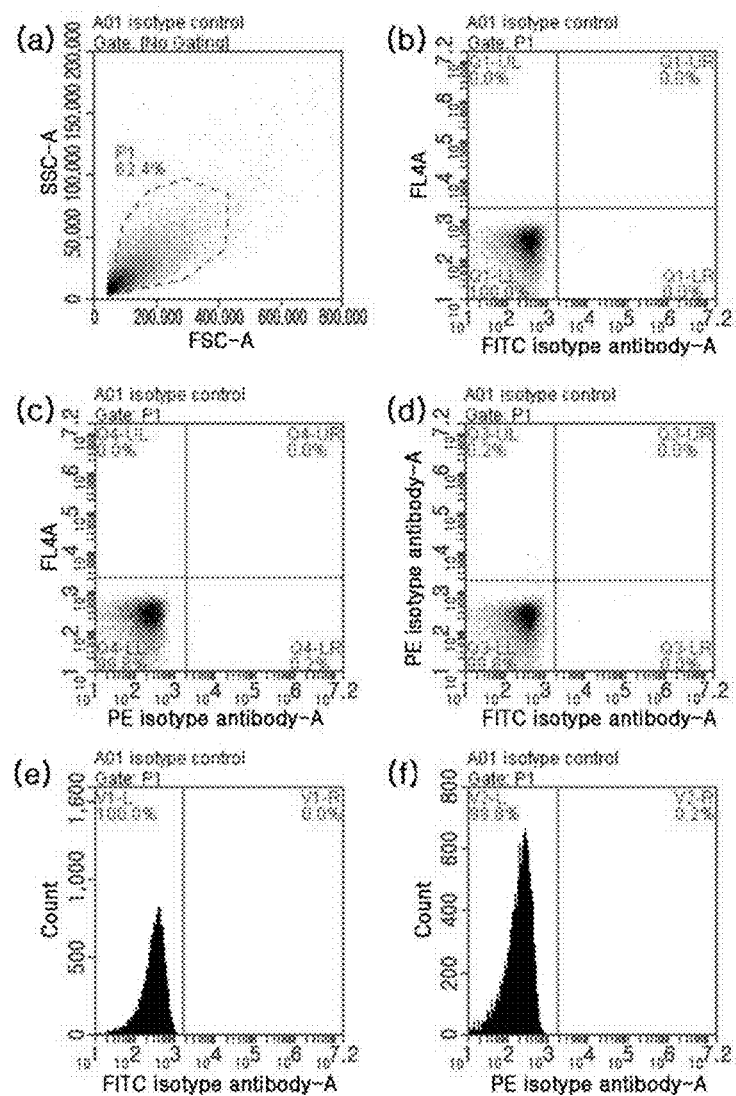
FIG. 5 is the result of flow cytometry for control staining 2 weeks after preservation in case 1.
Figure 6:
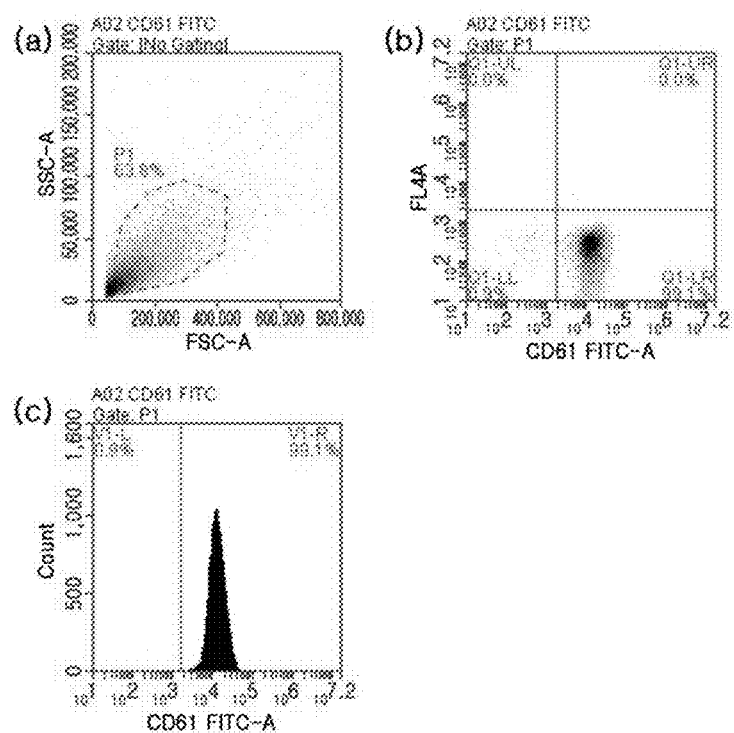
FIG. 6 is the result of flow cytometry for CD61 2 weeks after preservation in case 1.
Figure 7:
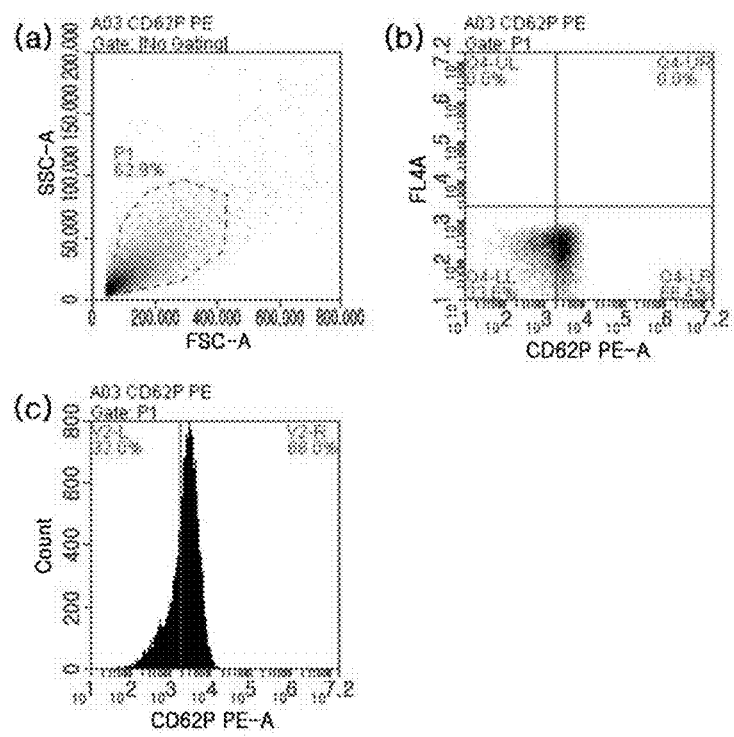
FIG. 7 is the result of flow cytometry for CD62P 2 weeks after preservation in case 1.
Figure 8:
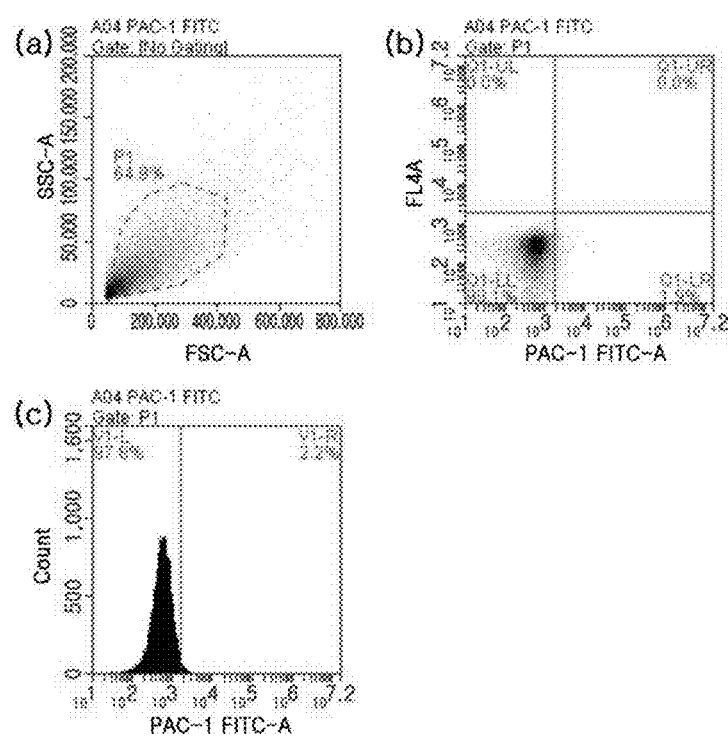
FIG. 8 is the result of flow cytometry for PAC-1 2 weeks after preservation in case 1.

Flow cytometry for control staining using an isotype monoclonal antibody at preservation initiation in case 1 was conducted, and the result was shown in FIG. 1. FIG. 2 to FIG. 4 show the results of flow cytometry for CD61, CD62P and PAC-1 at preservation initiation in case 1, respectively.

For example, as shown in FIG. 1(a), the region corresponding to the platelet location in the FSC and SSC screen was analyzed by gating, and as shown in FIG. 1(b) to FIG. 1(f), a set-marker was set to the each confirmed negative control group and the positive rate (%) was calculated as shown in FIG. 2 to FIG. 4.

Figure 9:
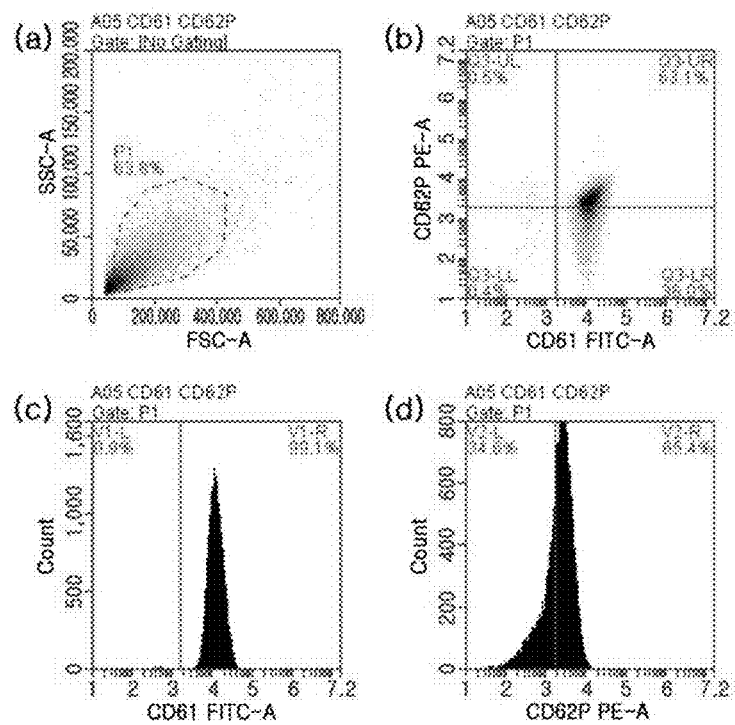
FIG. 9 is the result of flow cytometry for CD61 and CD62P 2 weeks after preservation in case 1.

Meanwhile, flow cytometry for control staining, CD61, CD62P and PAC-1 2 weeks after preservation was further conducted in the same manner, and the results are shown in FIG. 5 to FIG. 8, respectively. FIG. 9 shows the result of flow cytometry for concurrent expression of CD61 and CD62P 2 weeks after preservation in case 1.

When comparing the results of flow cytometry when starting preservation and 2 weeks after preservation, in the case of preserving platelets using the activated platelet preservation composition of the present invention for 2 weeks or longer, it can be confirmed that platelets positive for the cell markers, CD61 and CD62P, and negative for the PAC-1 are obtained from platelets mostly positive for only the cell marker, CD61, at the preservation initiation. And it can be confirmed that the PAC-1 positive rate (%) is less than 3% of the total platelets, and expression of the PAC-1 is inhibited in most platelets.

Test Example 6

Figure 10:
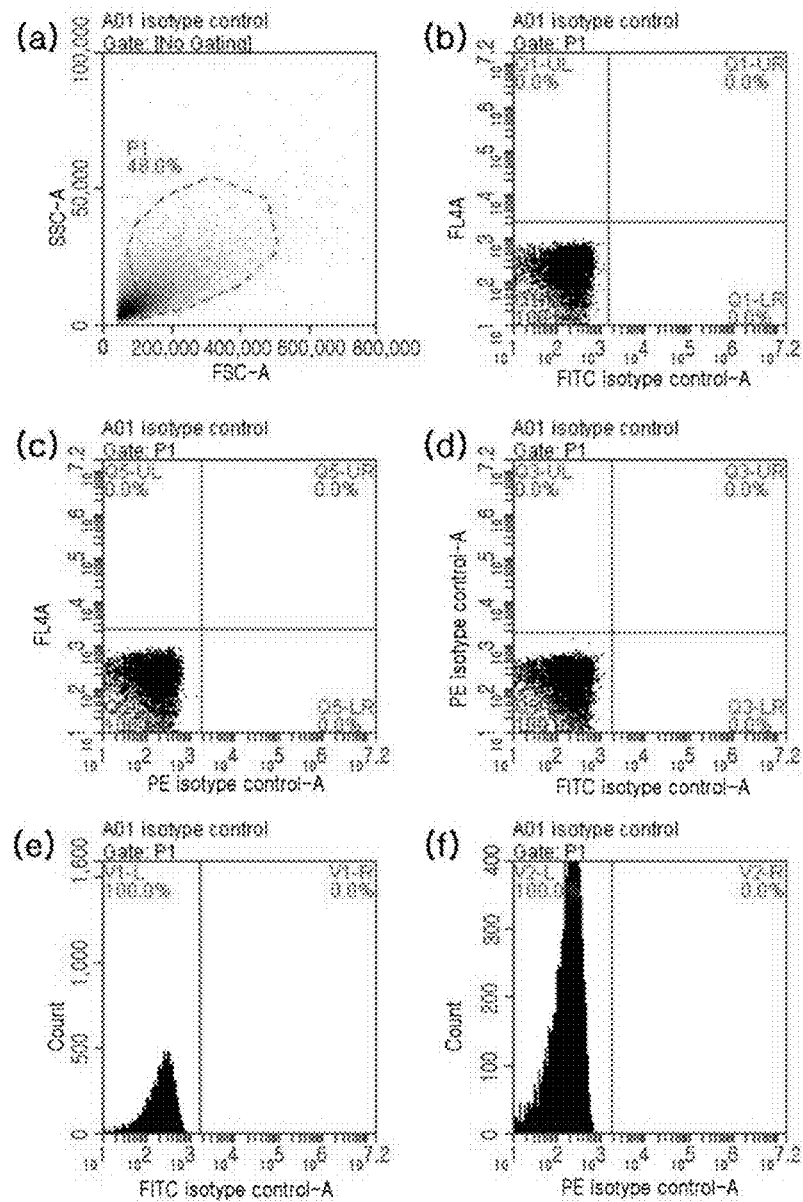
FIG. 10 is the result of flow cytometry for control staining at preservation initiation in case 2.
Figure 11:
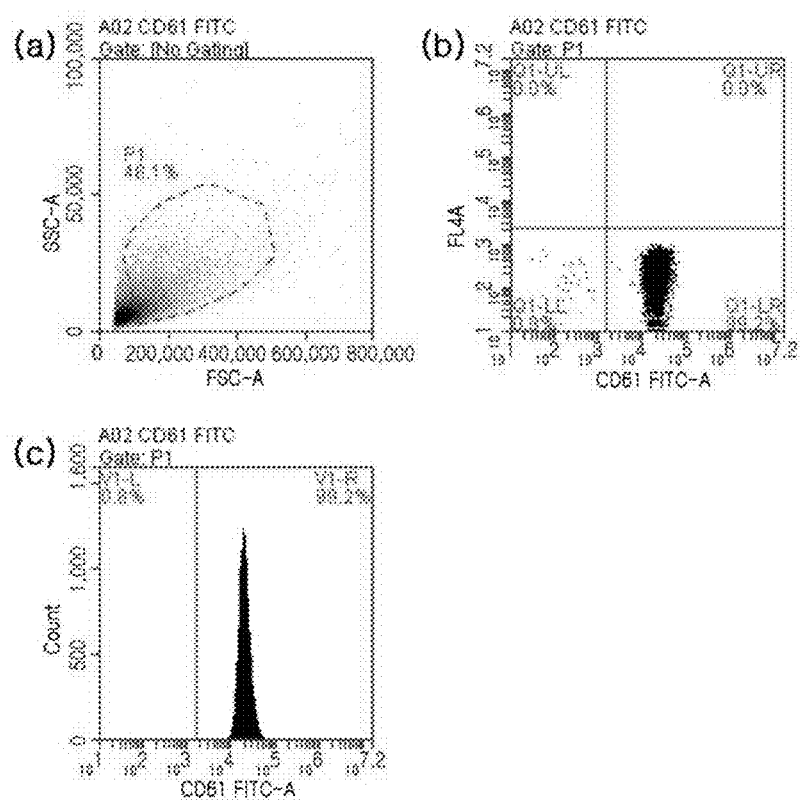
FIG. 11 is the result of flow cytometry for CD61 at preservation initiation in case 2.
Figure 12:
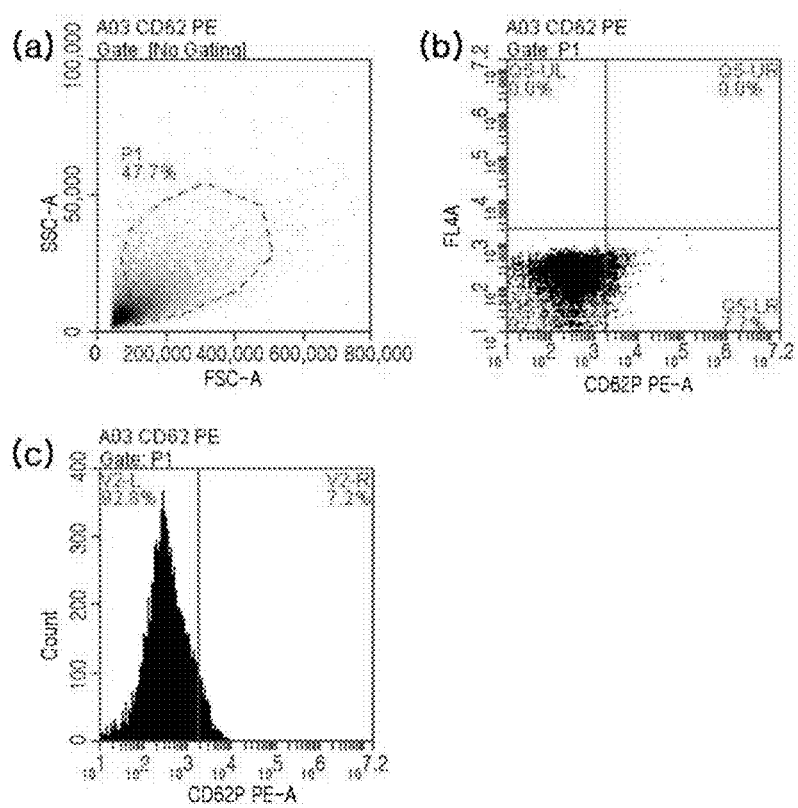
FIG. 12 is the result of flow cytometry for CD62P at preservation initiation in case 2.
Figure 13:
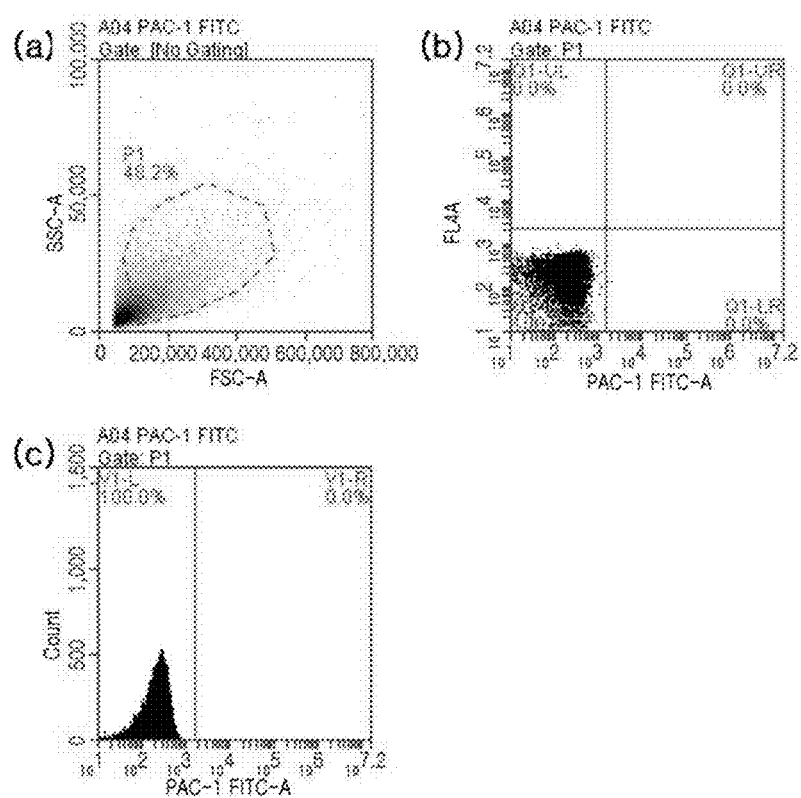
FIG. 13 is the result of flow cytometry for PAC-1 at preservation initiation in case 2.
Figure 14:
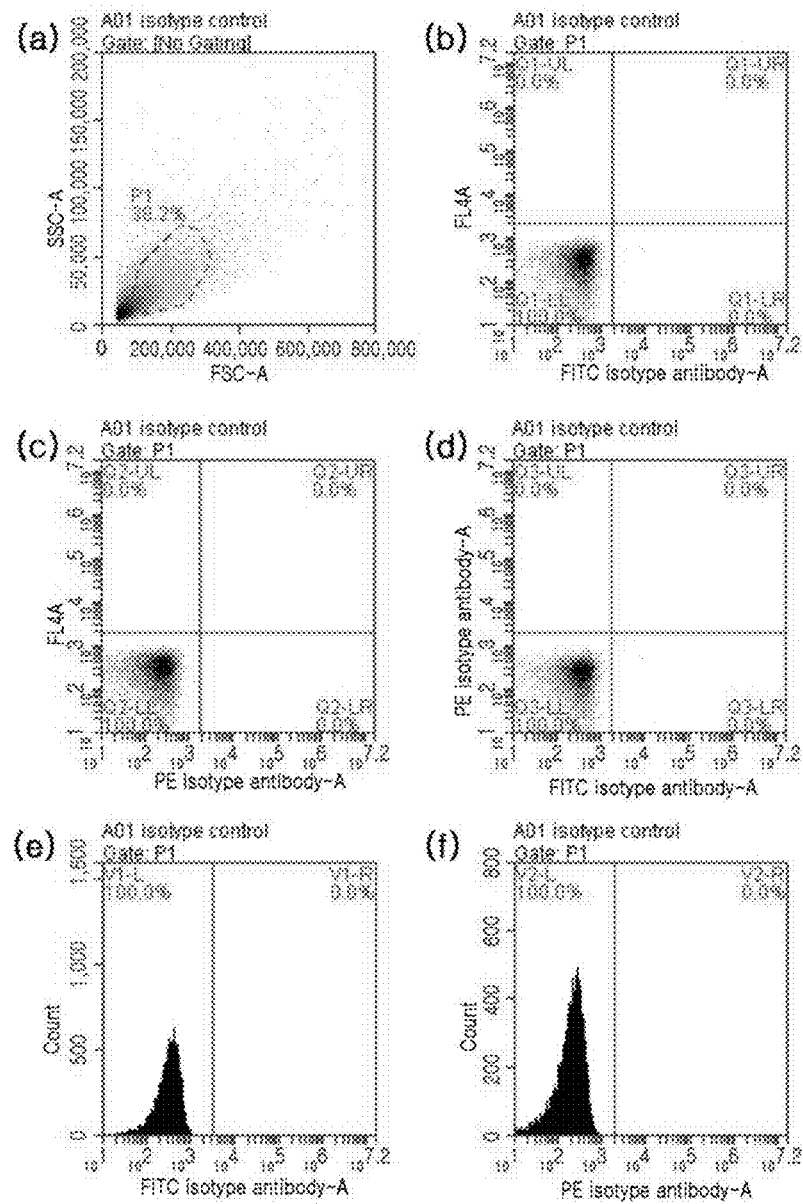
FIG. 14 is the result of flow cytometry for control staining 2 weeks after preservation in case 2.
Figure 15:
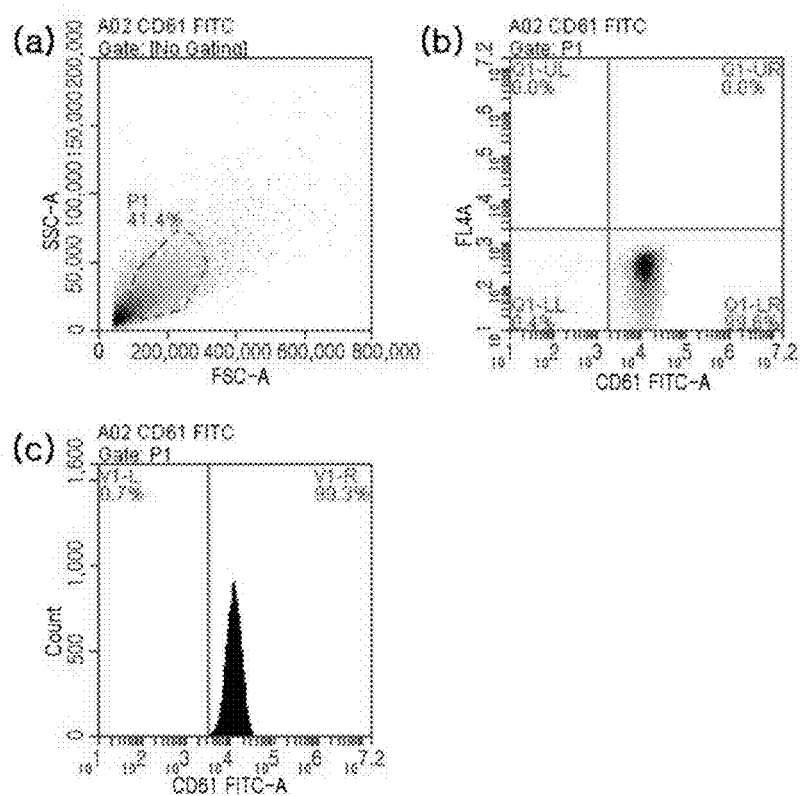
FIG. 15 is the result of flow cytometry for CD61 2 weeks after preservation in case 2.
Figure 16:
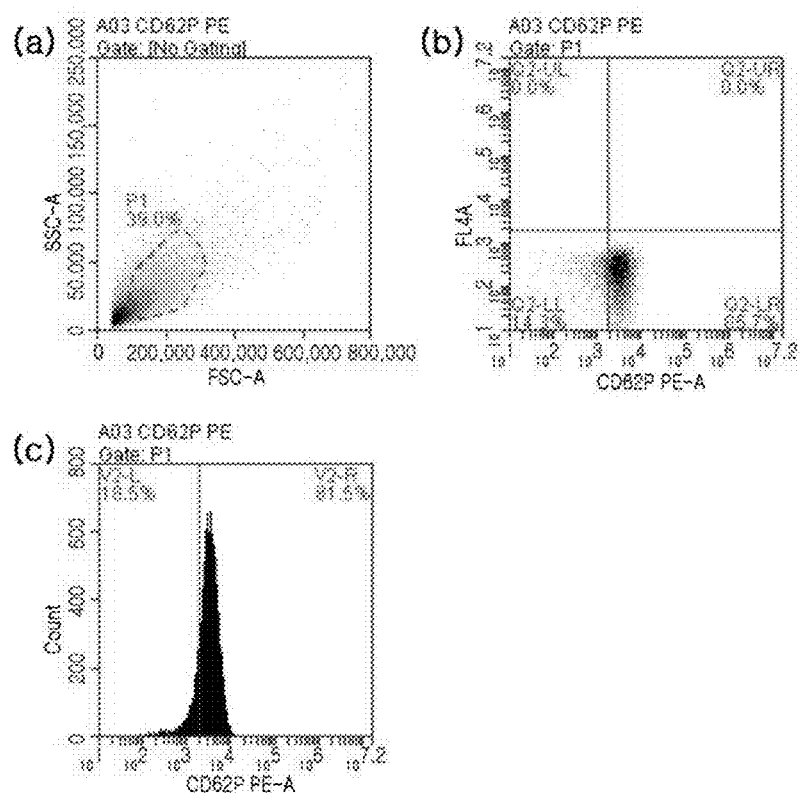
FIG. 16 is the result of flow cytometry for CD62P 2 weeks after preservation in case 2.
Figure 17:
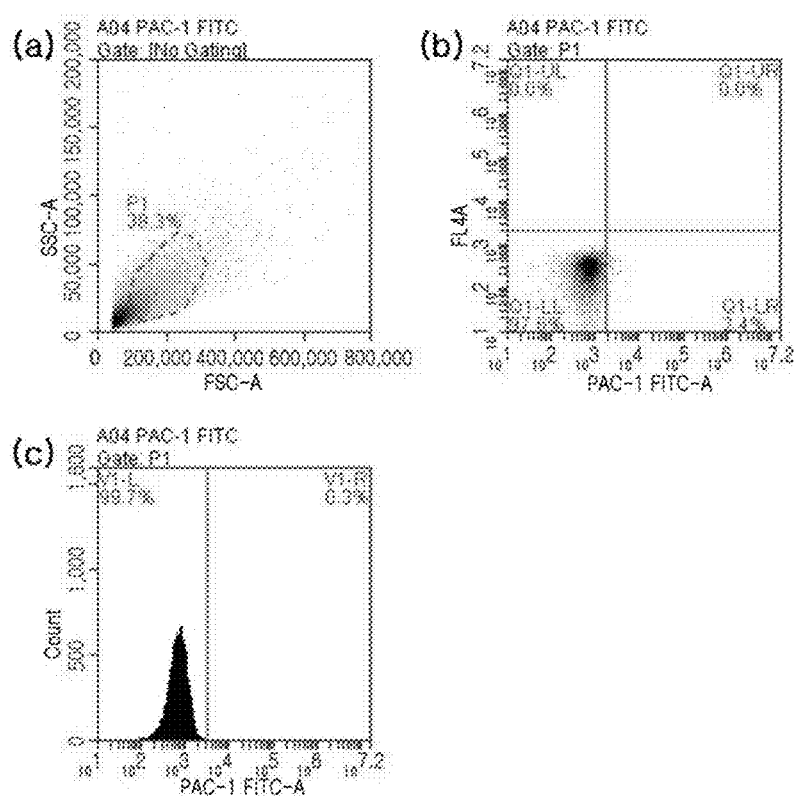
FIG. 17 is the result of flow cytometry for PAC-1 2 weeks after preservation in case 2.

Flow cytometry for control staining using an isotype monoclonal antibody at preservation initiation in case 2 was conducted, and the result was shown in FIG. 10. FIG. 11 to FIG. 13 show the results of flow cytometry for CD61, CD62P and PAC-1 at preservation initiation in case 1, respectively.

For example, as shown in FIG. 10(a), the region corresponding to the platelet location in the FSC and SSC screen was analyzed by gating, and as shown in FIG. 10(b) to FIG. 10(f), a set-marker was set to the each confirmed negative control group and the positive rate (%) was calculated as shown in FIG. 11 to FIG. 13.

Figure 18:
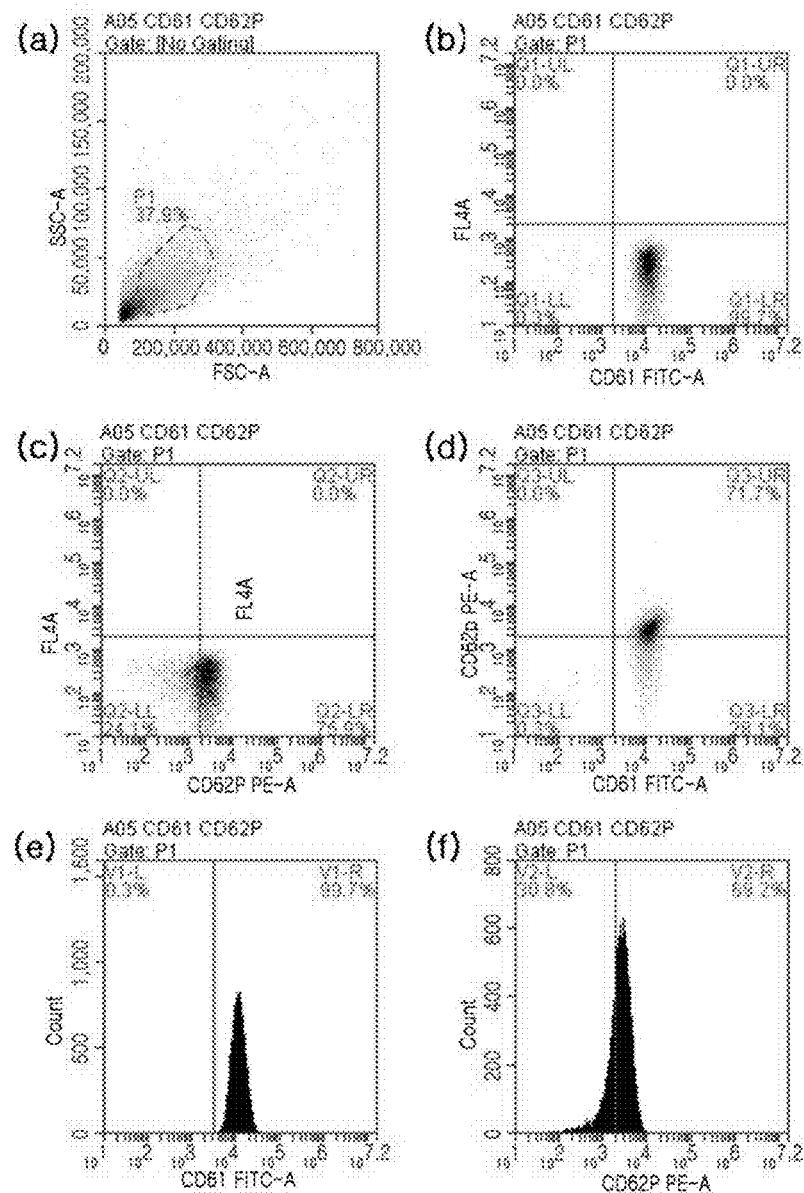
FIG. 18 is the result of flow cytometry for CD61 and CD62P 2 weeks after preservation in case 2.

Meanwhile, flow cytometry for control staining, CD61, CD62P and PAC-1 2 weeks after preservation was further conducted in the same manner, and the results are shown in FIG. 14 to FIG. 17, respectively. FIG. 18 shows the result of flow cytometry for concurrent expression of CD61 and CD62P 2 weeks after preservation in case 1.

When comparing the results of flow cytometry when starting preservation and 2 weeks after preservation, in the case of preserving platelets using the activated platelet preservation composition of the present invention for 2 weeks or longer, it can be confirmed that platelets positive for the cell markers, CD61 and CD62P, and negative for the PAC-1 are obtained from platelets mostly positive for only the cell marker, CD61, at the preservation initiation. And it can be confirmed that PAC-1 positive rate (%) is less than 3% of the total platelets, and expression of the PAC-1 is inhibited in most platelets.

Test Example 7

Figure 19:
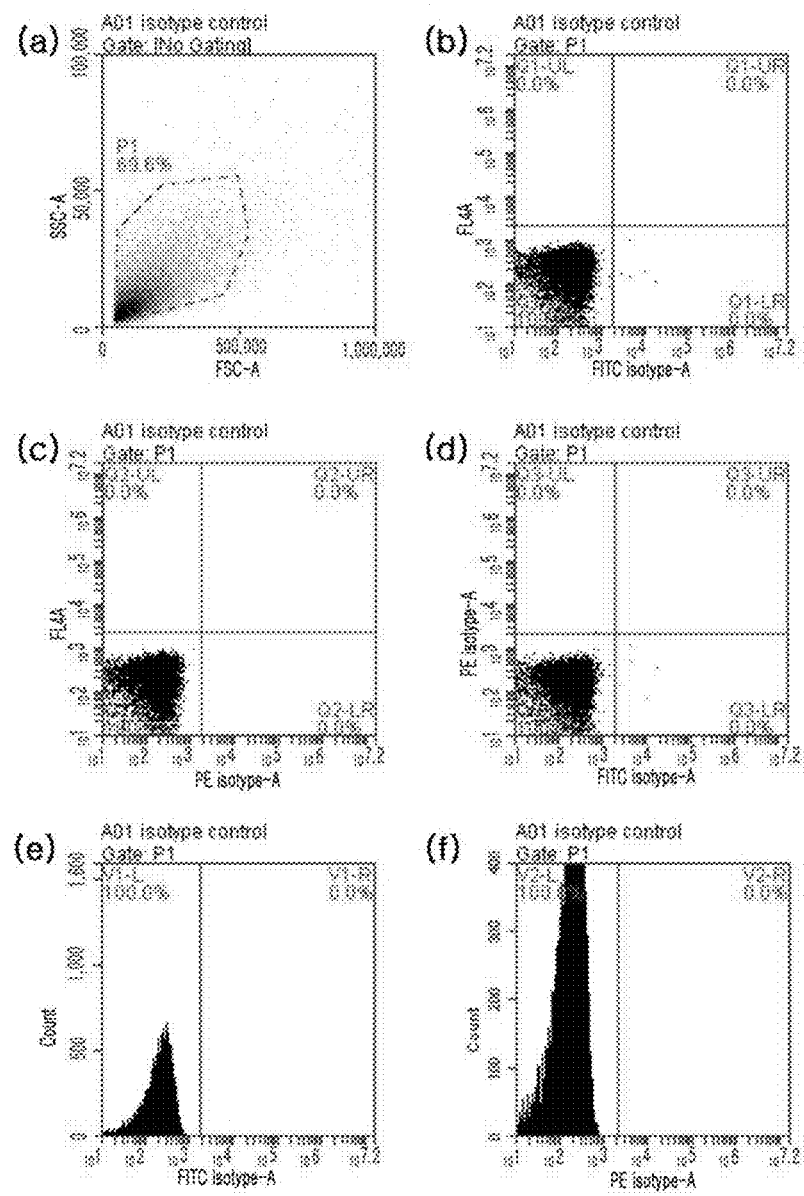
FIG. 19 is the result of flow cytometry for control staining at preservation initiation in case 3.
Figure 20:
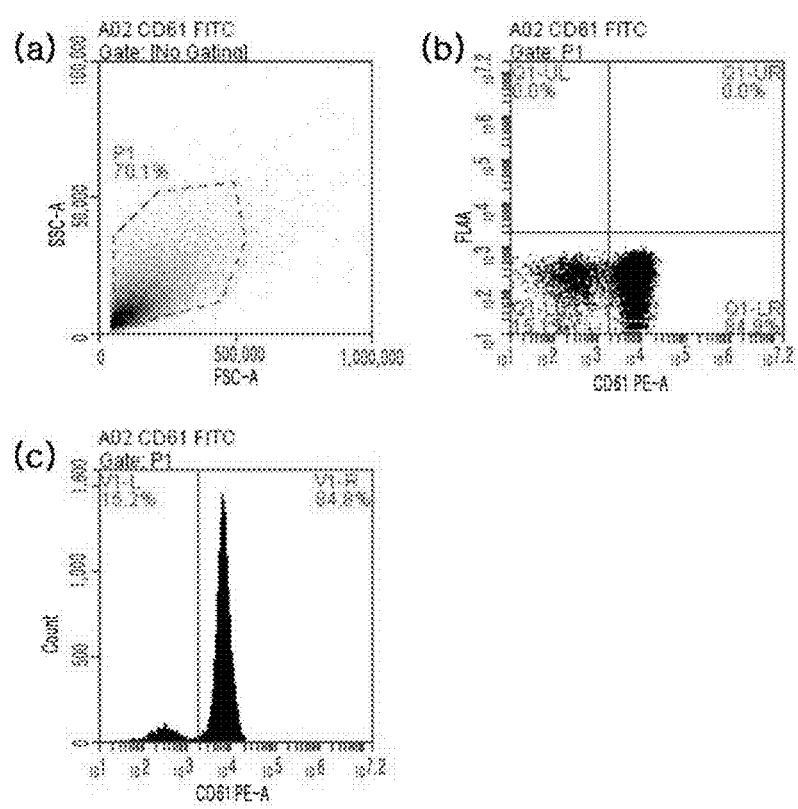
FIG. 20 is the result of flow cytometry for CD61 at preservation initiation in case 3.
Figure 21:
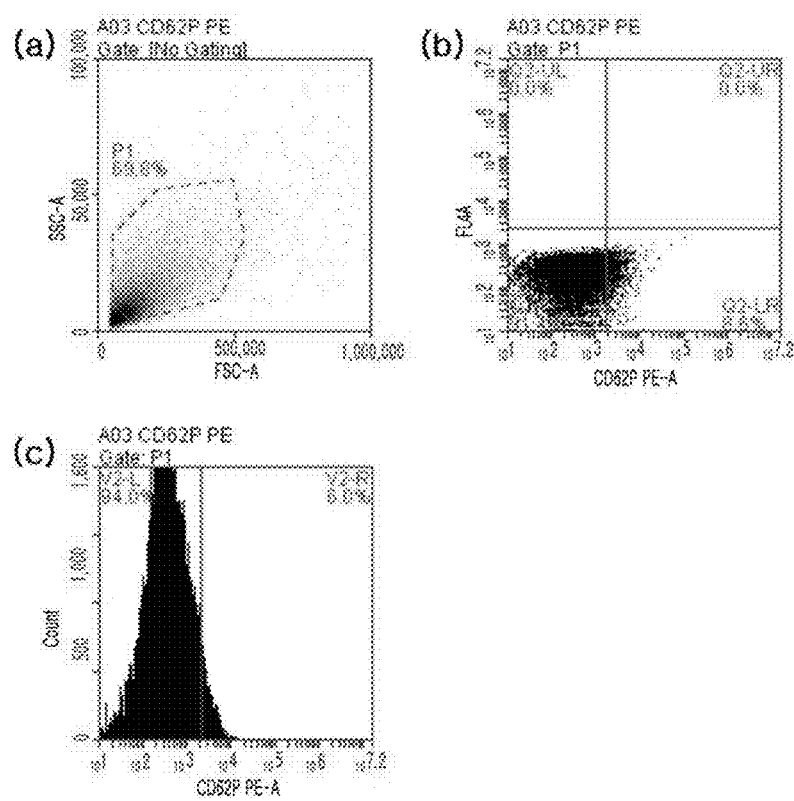
FIG. 21 is the result of flow cytometry for CD62P at preservation initiation in case 3.
Figure 22:
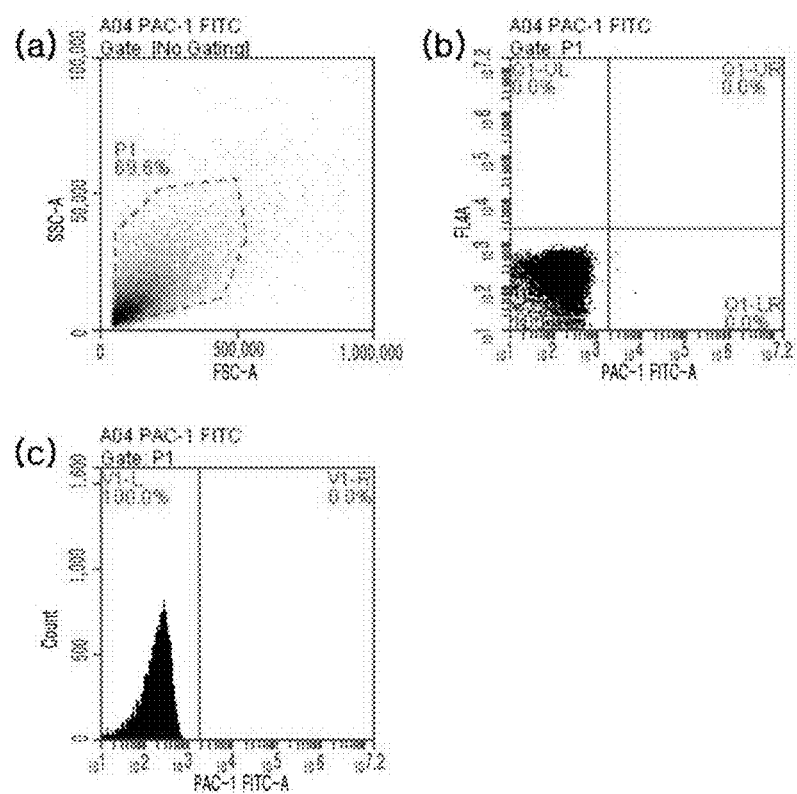
FIG. 22 is the result of flow cytometry for PAC-1 at preservation initiation in case 3.
Figure 23:
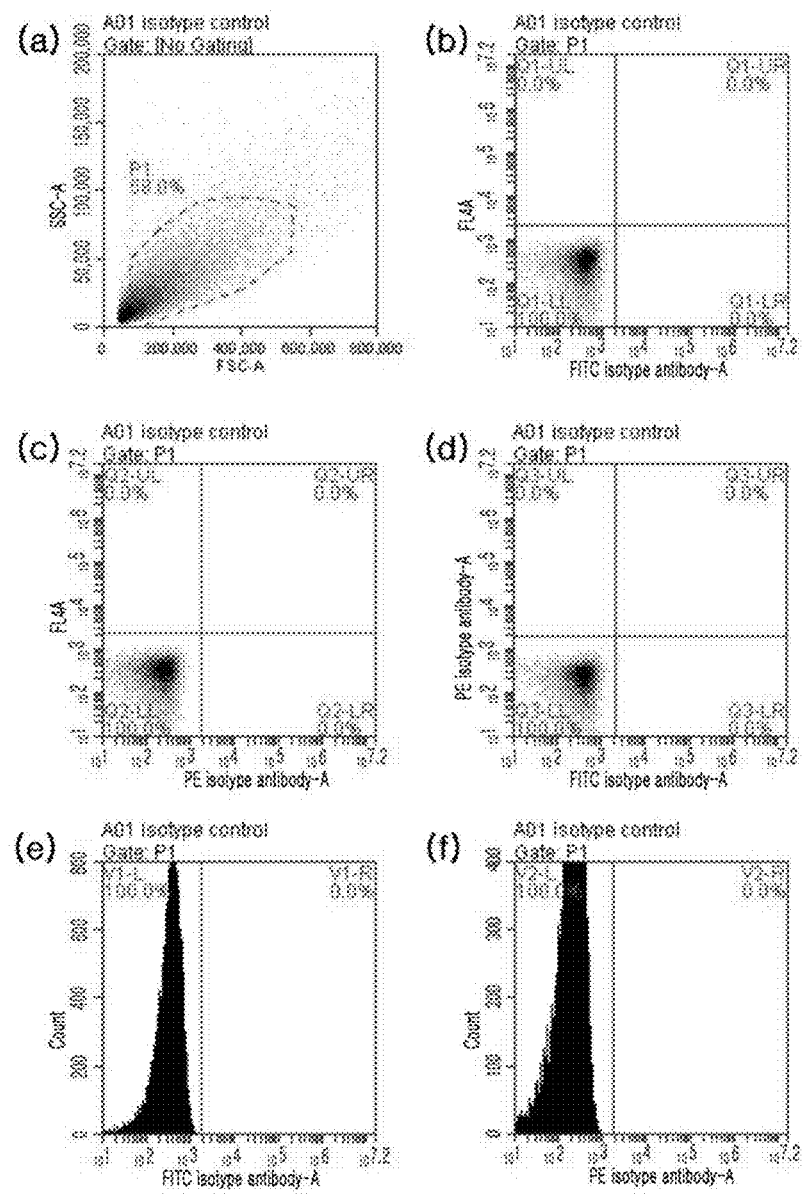
FIG. 23 is the result of flow cytometry for control staining 2 weeks after preservation in case 3.
Figure 24:
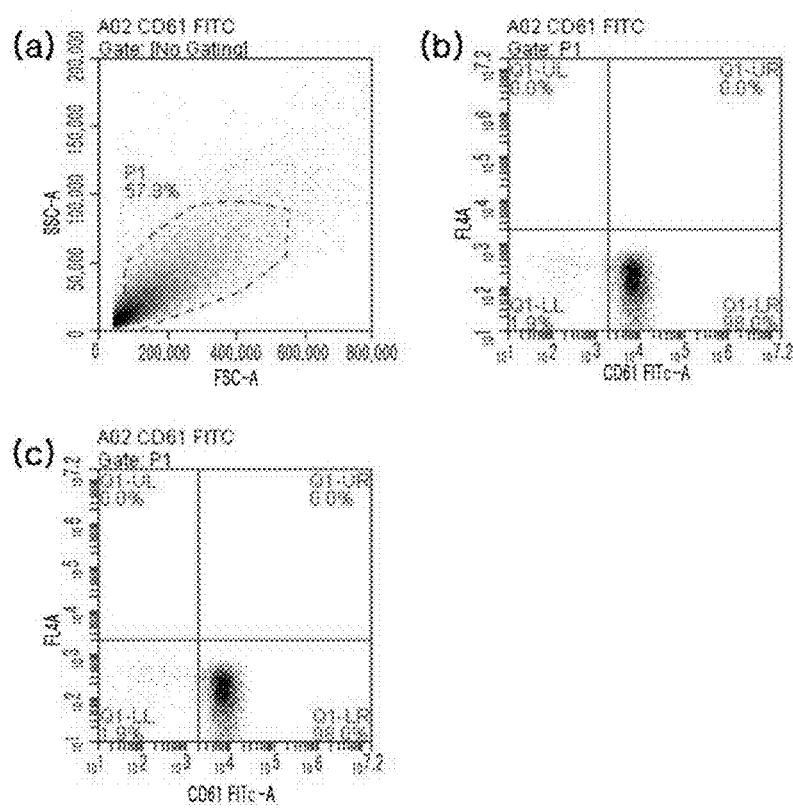
FIG. 24 is the result of flow cytometry for CD61 2 weeks after preservation in case 3.
Figure 25:
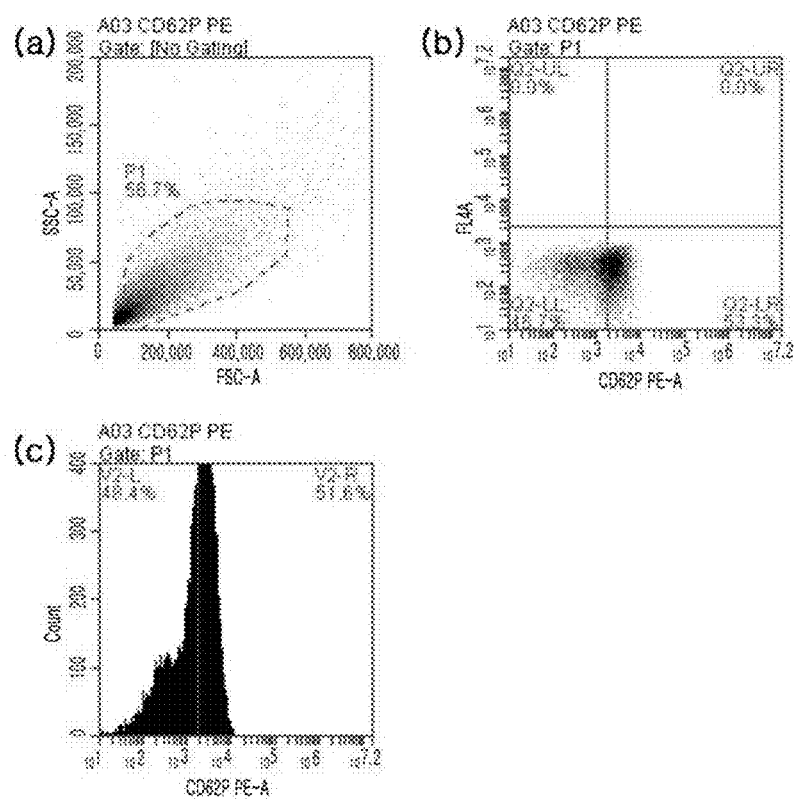
FIG. 25 is the result of flow cytometry for CD62P 2 weeks after preservation in case 3.
Figure 26:
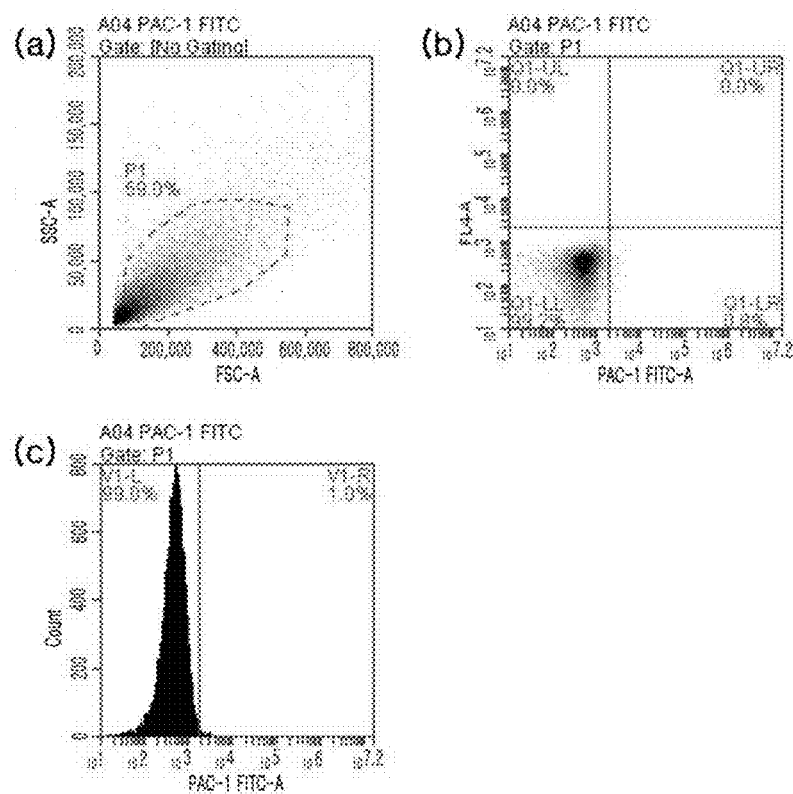
FIG. 26 is the result of flow cytometry for PAC-1 2 weeks after preservation in case 3.

Flow cytometry for control staining using an isotype monoclonal antibody at preservation initiation in case 3 was conducted, and the result was shown in FIG. 19. FIG. 20 to FIG. 22 show the results of flow cytometry for CD61, CD62P and PAC-1 at preservation initiation in case 1, respectively.

For example, as shown in FIG. 19(a), the region corresponding to the platelet location in the FSC and SSC screen was analyzed by gating, and as shown in FIG. 19(b) to FIG. 19(f), a set-marker was set to the each confirmed negative control group and the positive rate (%) was calculated as shown in FIG. 20 to FIG. 22.

Figure 27:
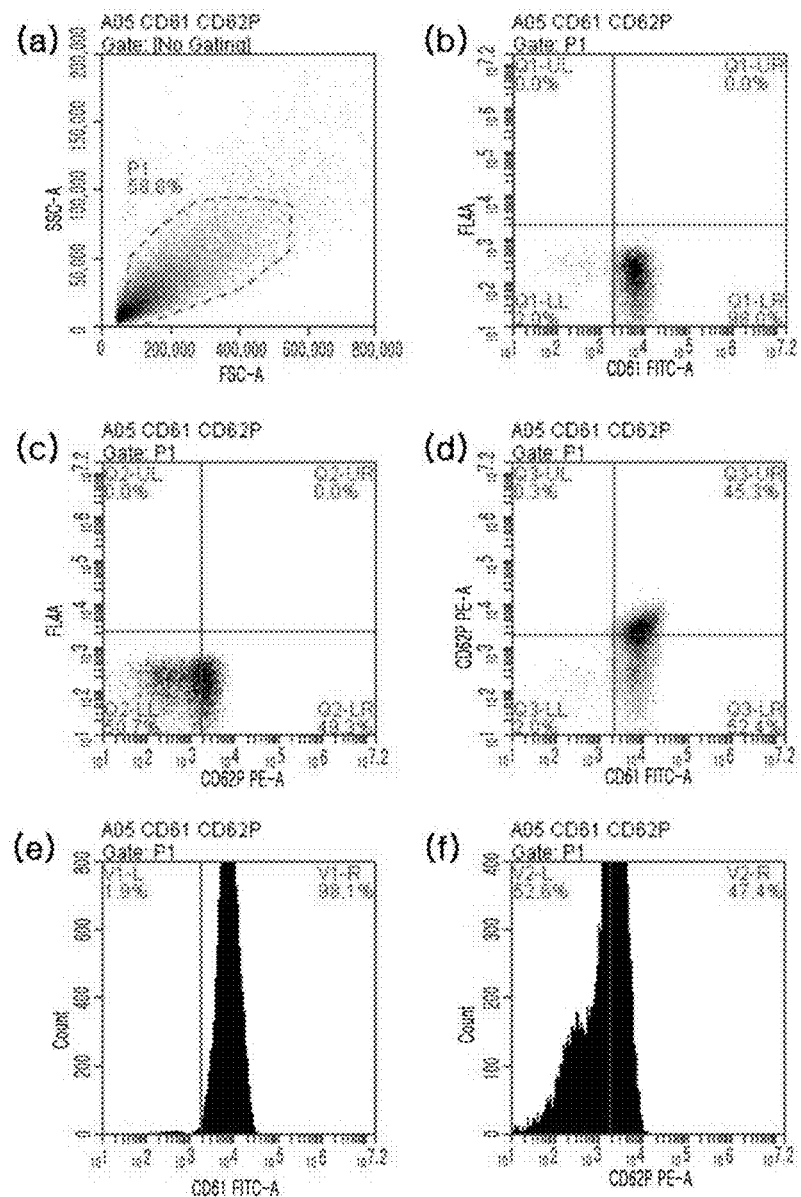
FIG. 27 is the result of flow cytometry for CD61 and CD62P 2 weeks after preservation in case 3.

Meanwhile, flow cytometry for control staining, CD61, CD62P and PAC-1 2 weeks after preservation was further conducted in the same manner, and the results are shown in FIG. 23 to FIG. 26, respectively. FIG. 27 shows the result of flow cytometry for concurrent expression of CD61 and CD62P 2 weeks after preservation in case 1.

When comparing the results of flow cytometry when starting preservation and 2 weeks after preservation, in the case of preserving platelets using the activated platelet preservation composition of the present invention for 2 weeks or longer, it can be confirmed that platelets positive for the cell markers, CD61 and CD62P, and negative for the PAC-1 is obtained from platelets mostly positive for only the cell marker, CD61, at the preservation initiation. And it can be confirmed that PAC-1 positive rate (%) is less than 3% of the total platelets, and expression of the PAC-1 is inhibited in most of platelets.

Test Example 8

Figure 28:
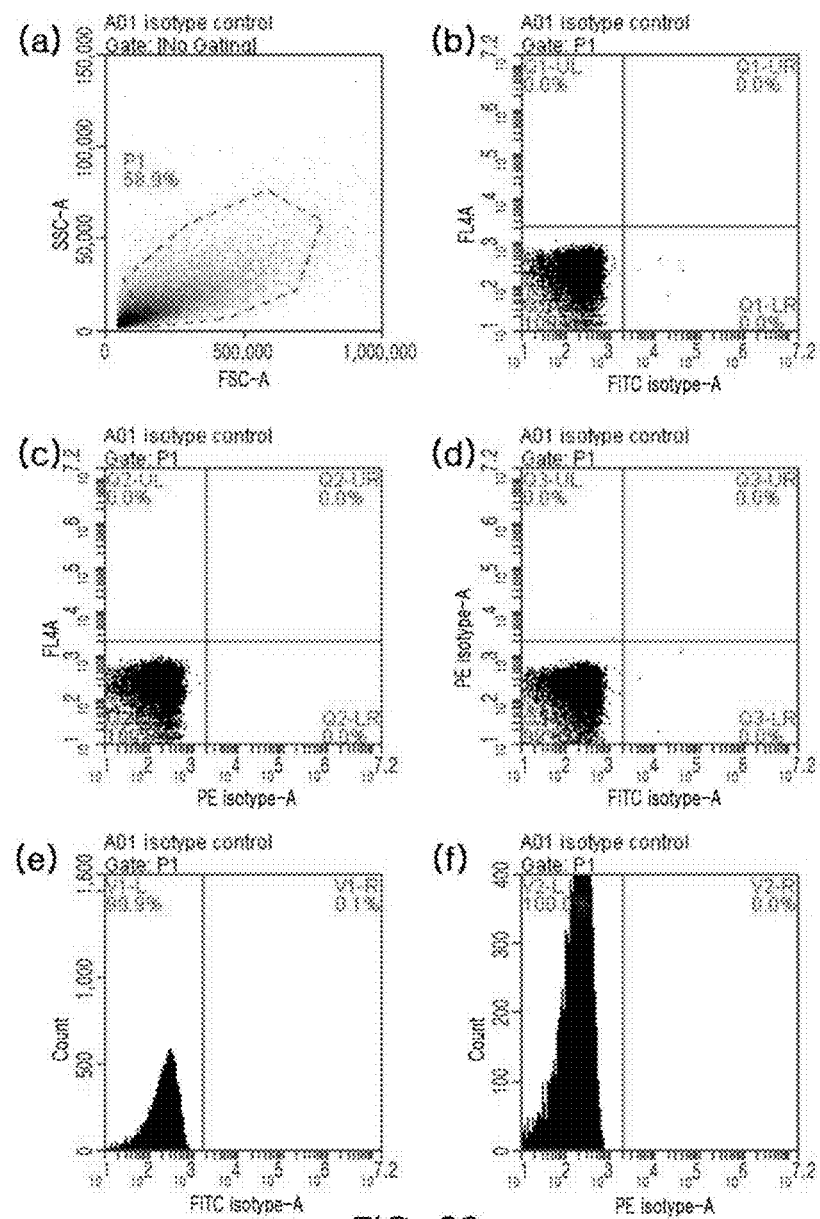
FIG. 28 is the result of flow cytometry for control staining at preservation initiation in case 4.
Figure 29:
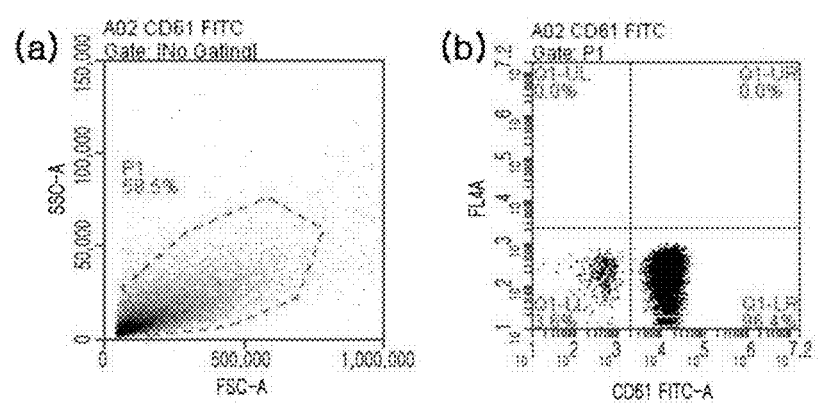
FIG. 29 is the result of flow cytometry for CD61 at preservation initiation in case 4.
Figure 30:
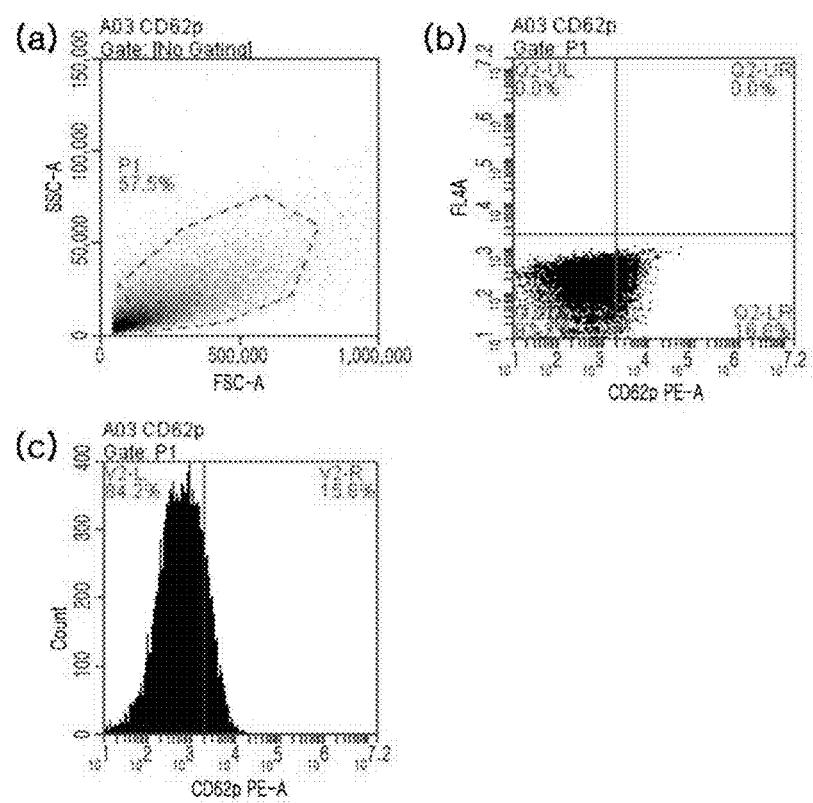
FIG. 30 is the result of flow cytometry for CD62P at preservation initiation in case 4.
Figure 31:
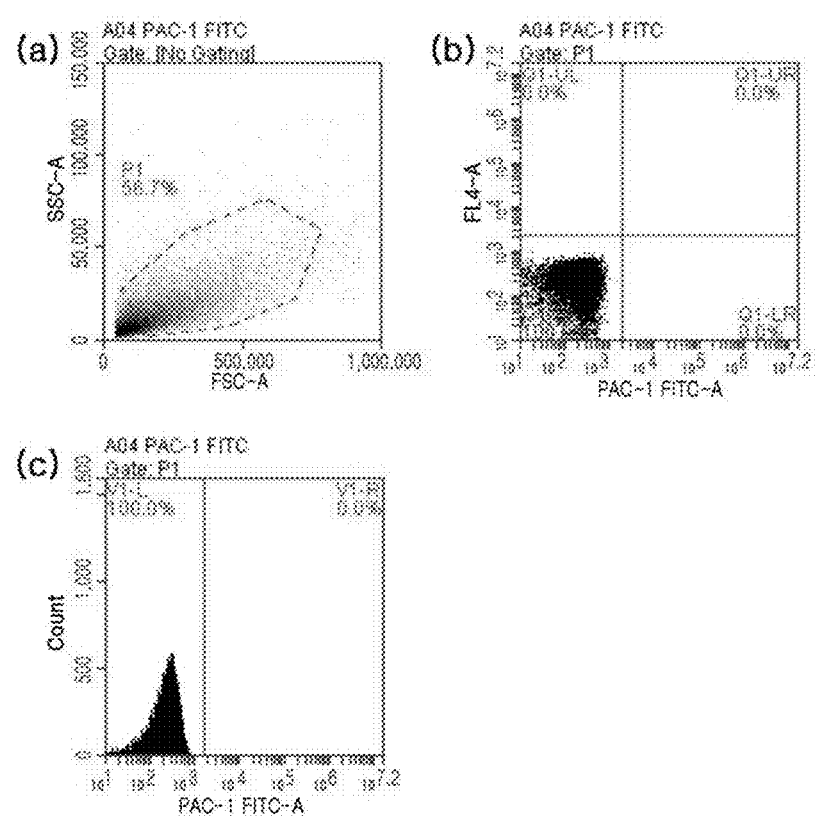
FIG. 31 is the result of flow cytometry for PAC-1 at preservation initiation in case 4.
Figure 32:
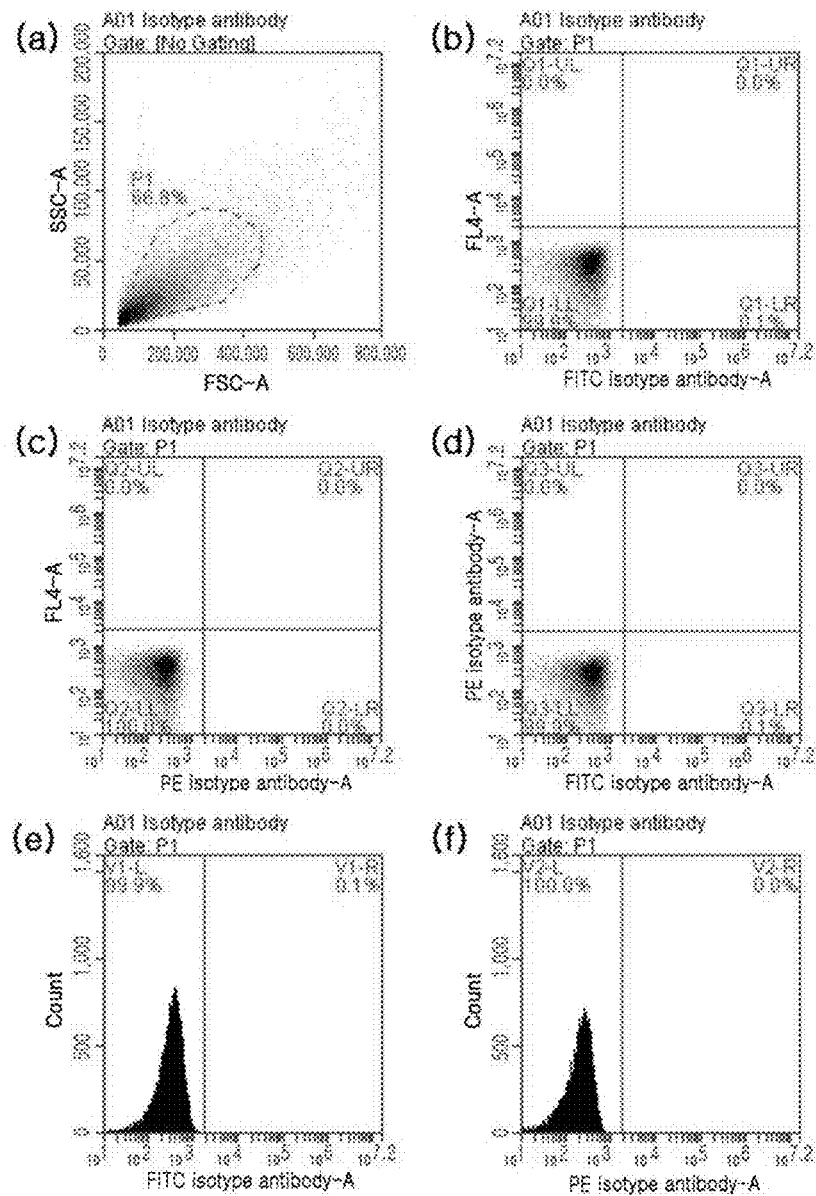
FIG. 32 is the result of flow cytometry for control staining 2 weeks after preservation in case 4.
Figure 33:
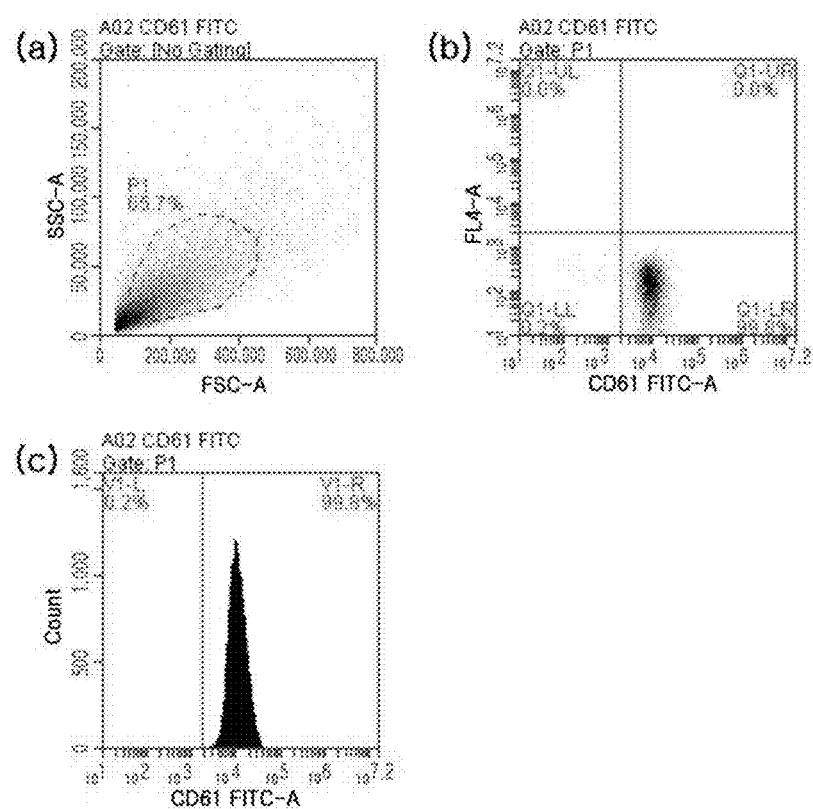
FIG. 33 is the result of flow cytometry for CD61 2 weeks after preservation in case 4.
Figure 34:
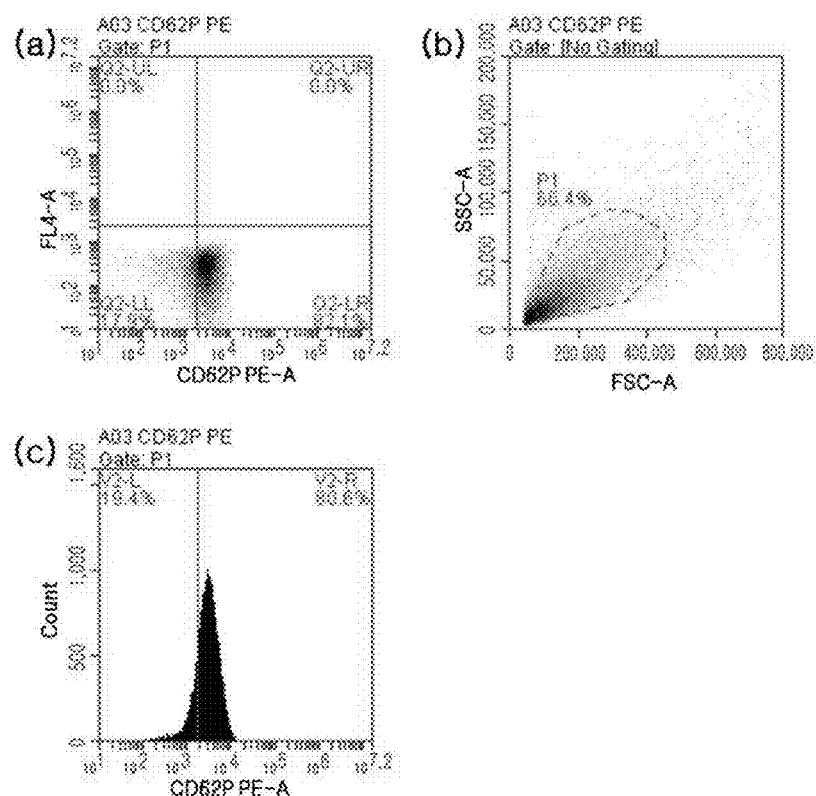
FIG. 34 is the result of flow cytometry for CD62P 2 weeks after preservation in case 4.
Figure 35:
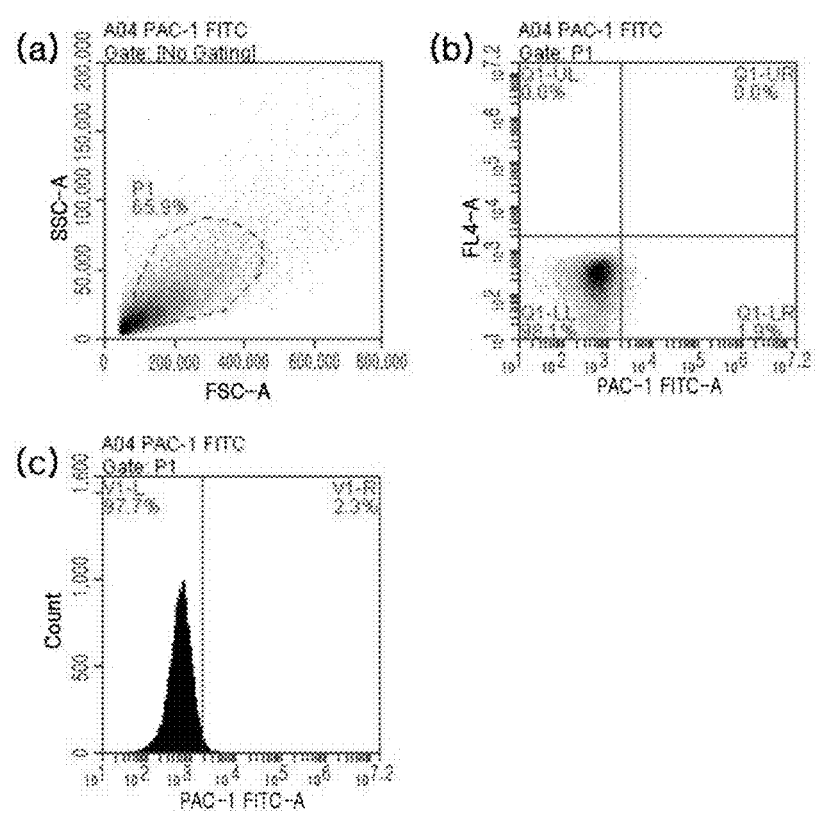
FIG. 35 is the result of flow cytometry for PAC-1 2 weeks after preservation in case 4.

Flow cytometry for control staining using an isotype monoclonal antibody at preservation initiation in case 4 was conducted, and the result was shown in FIG. 28. FIG. 29 to FIG. 31 show the results of flow cytometry for CD61, CD62P and PAC-1 at preservation initiation in case 1, respectively.

For example, as shown in FIG. 28(a), the region corresponding to the platelet location in the FSC and SSC screen was analyzed by gating, and as shown in FIG. 28(b) to FIG. 28(f), a set-marker was set to the each confirmed negative control group and the positive rate (%) was calculated as shown in FIG. 29 to FIG. 31.

Figure 36:
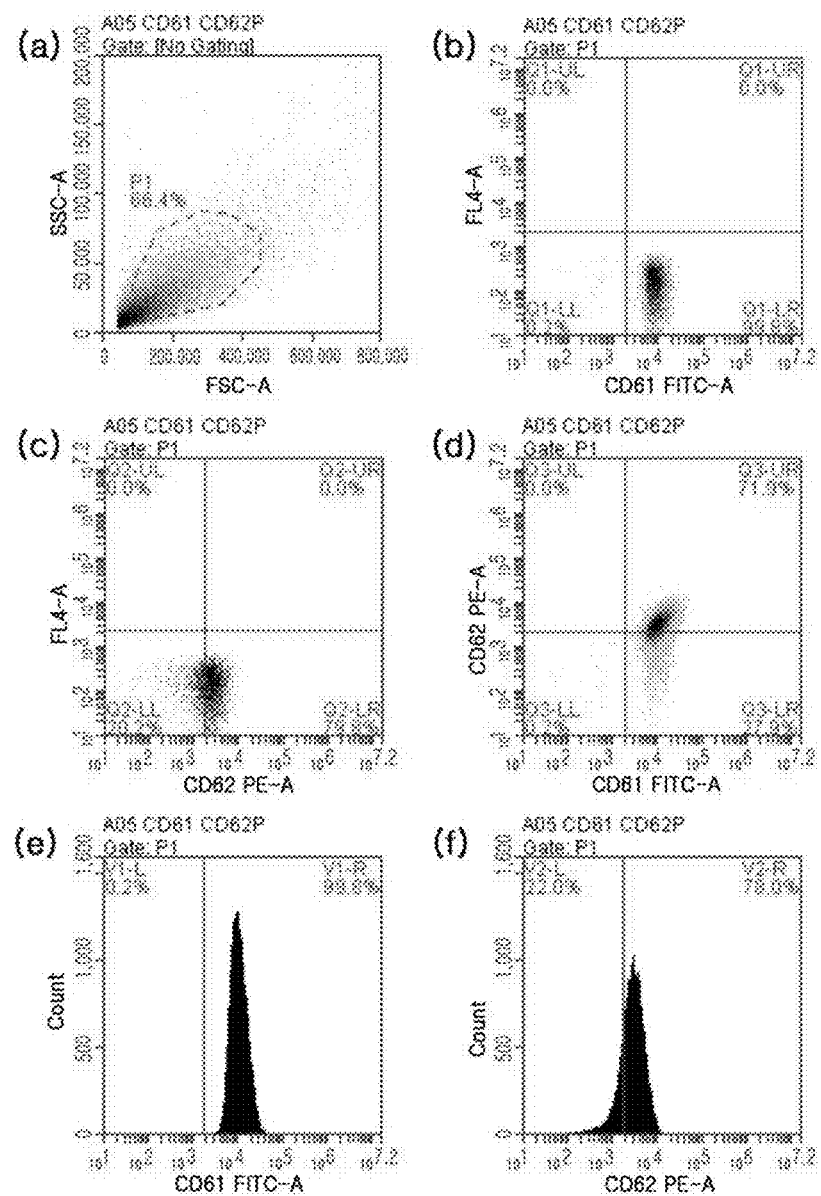
FIG. 36 is the result of flow cytometry for CD61 and CD62P 2 weeks after preservation in case 4.

Meanwhile, flow cytometry for control staining, CD61, CD62P and PAC-1 2 weeks after preservation was further conducted in the same manner, and the results are shown in FIG. 32 to FIG. 35, respectively. FIG. 36 shows the result of flow cytometry for concurrent expression of CD61 and CD62P 2 weeks after preservation in case 1.

When comparing the results of flow cytometry when starting preservation and 2 weeks after preservation, in the case of preserving platelets using the activated platelet preservation composition of the present invention for 2 weeks or longer, it can be confirmed that platelets positive for the cell markers, CD61 and CD62P, and negative for the PAC-1 are obtained from platelets mostly positive for only the cell marker, CD61, at the preservation initiation. And it can be confirmed that PAC-1 positive rate (%) is less than 3% of the total platelets, and expression of the PAC-1 is inhibited in most platelets.

(3) Conclusion

The results of Test Examples 5 to 8 were summarized as shown in the following Table 4. Like this, in the case of using the activated platelet preservation composition of the present invention, platelets, which could not be preserved for 5 days or longer in the past, can be preserved for an extended period of time innovatively, and in addition, it can be confirmed that platelets preserved like this are the activated platelets positive expressing the cell markers, CD61 and CD62P, and not expressing the PAC-1.

TABLE 4

| | Time of Analysis | CD61 Positive Rate (%) | CD62P Positive Rate (%) | PAC-1 Positive Rate (%) | CD61 and CD62P Concurrent Positive Rate (%) |
|---|---|---|---|---|---|
| Test Example 5 | 0 Week (When starting preservation) | 99.2 | 1.4 | 0.1 | |
| | After 2 weeks | 99.1 | 68.0 | 2.2 | 63.1 |
| Test Example 6 | 0 Week (When starting preservation) | 99.2 | 7.2 | 0.0 | |
| | After 2 weeks | 99.3 | 81.5 | 0.3 | 71.7 |
| Test Example 7 | 0 Week (When starting preservation) | 84.8 | 6.0 | 0.0 | |
| | After 2 weeks | 98.0 | 51.6 | 1.0 | 45.3 |
| Test Example 8 | 0 Week (When starting preservation) | 96.4 | 15.8 | 0.0 | |
| | After 2 weeks | 99.8 | 80.6 | 2.3 | 71.9 |

According to the present invention, an activated platelet preservation composition, which enables to inhibit platelet destruction and maintain spontaneous activation, is provided. Here, in the case of using the activated platelet preservation composition of the present invention, platelets, which are positive for a platelet marker, CD61, and an activation marker, CD62P (p-selectin) and negative for PAC-1 among cell markers, can be obtained. Therefore, the activated platelets can be used while preserving for an extended period of time.

While exemplary embodiments have been shown and described above, it will be apparent to those skilled in the art that modifications and variations could be made without departing from the spirit and scope of the present disclosure as defined by the appended claims.

What is claimed is:

1. A method for preserving an activated platelet, comprising:
   mixing blood with an anticoagulant and then centrifuging thereof to obtain platelet rich plasma and plasma;
   injecting the platelet rich plasma and the plasma obtained above into a sterilized airtight container, which contains an activated platelet preservation composition comprising a divalent cation, chloride, vitamin B, a selenium source and a solvent and whose internal pressure is equalized with external pressure; and
   preserving the container into which the platelet rich plasma and the plasma are injected at a temperature of 35° C. to 38° C.,
   wherein the preserved activated platelet is positive for CD61 and CD62P (P-Selectin) cell markers, and negative for a PAC-1 cell marker.

2. The method for preserving an activated platelet of claim 1, the preserving is maintained for 14 days or more.

* * * * *